United States Patent
Kakegawa et al.

(10) Patent No.: US 10,017,487 B2
(45) Date of Patent: Jul. 10, 2018

(54) FUSED HETEROCYCLIC COMPOUND

(71) Applicant: Takeda Pharmaceutical Company Limited, Chuo-ku, Osaka-shi, Osaka (JP)

(72) Inventors: Keiko Kakegawa, Kanagawa (JP); Zenichi Ikeda, Kanagawa (JP); Minoru Sasaki, Kanagawa (JP); Fumiaki Kikuchi, Kanagawa (JP); Yoichi Nishikawa, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 15/561,613

(22) PCT Filed: Mar. 25, 2016

(86) PCT No.: PCT/JP2016/059705
§ 371 (c)(1),
(2) Date: Sep. 26, 2017

(87) PCT Pub. No.: WO2016/158788
PCT Pub. Date: Oct. 6, 2016

(65) Prior Publication Data
US 2018/0072694 A1    Mar. 15, 2018

(30) Foreign Application Priority Data

Mar. 27, 2015 (JP) ................. 2015-066622

(51) Int. Cl.
*C07D 307/79* (2006.01)
*C07F 9/655* (2006.01)
*C07D 413/04* (2006.01)

(52) U.S. Cl.
CPC ......... *C07D 307/79* (2013.01); *C07D 413/04* (2013.01); *C07F 9/65517* (2013.01)

(58) Field of Classification Search
CPC .. C07D 307/79; C07D 413/04; C07F 9/65517
See application file for complete search history.

(56) References Cited

U.S. PATENT DOCUMENTS

| | | |
|---|---|---|
| 2012/0283222 A1 | 11/2012 | Konishi et al. |
| 2014/0094489 A1 | 4/2014 | Suzuki et al. |
| 2014/0378459 A1 | 12/2014 | Fujiyasu et al. |
| 2015/0225361 A1* | 8/2015 | Ikeda ............. C07D 307/81 514/469 |
| 2016/0031847 A1* | 2/2016 | Fujiyasu ......... C07D 307/81 514/307 |

FOREIGN PATENT DOCUMENTS

| | | |
|---|---|---|
| WO | WO 2009/071601 A1 | 6/2009 |
| WO | WO 2011/071048 A1 | 6/2011 |
| WO | WO 2012/169579 A1 | 12/2012 |
| WO | WO 2013/039187 A1 | 3/2013 |
| WO | WO 2013/187533 A1 | 12/2013 |
| WO | WO 2014/142219 A1 | 9/2014 |
| WO | WO 2015/122187 A1 | 8/2015 |
| WO | WO 2015/122188 A1 | 8/2015 |
| WO | WO 2016/104630 A1 | 6/2016 |
| WO | WO 2016/148135 A1 | 9/2016 |

OTHER PUBLICATIONS

M.E. Gasparian et al., 79 Protein Expression and Purification, 191-196 (2011).*
S. Braud et al., 2 Future Medicinal Chemistry, 1777-1783 (2010).*
L. Costantino et al., 7 Future Medicinal Chemistry, 315-336 (2015).*
S. Braud et al., 7 PLOS One, 1-7 (2012).*
M. Azhar et al., 45 Preparative Biochemistry & Biotechnology, 268-278 (2015).*
International Search Report dated Mar. 22, 2016, in PCT/JP2016/059705.

* cited by examiner

*Primary Examiner* — Alexander R Pagano
(74) *Attorney, Agent, or Firm* — Foley & Lardner LLP

(57) ABSTRACT

The present invention relates to a condensed heterocyclic compound that has an enteropeptidase inhibitory effect, and use of the compound as a medicament for the treatment or prevention of obesity, diabetes mellitus, or the like. Specifically, the present invention relates to a compound represented by the formula (I) or a salt thereof, and use of the compound as a medicament for the treatment or prevention of obesity, diabetes mellitus, or the like [in the formula, each symbol is as defined in the specification].

16 Claims, No Drawings

FUSED HETEROCYCLIC COMPOUND

TECHNICAL FIELD

Related Application

The present application claims the priority based on Japanese Patent Application No. 2015-066622 (filed on Mar. 27, 2015), the contents of which are incorporated herein by reference.

The present invention relates to a condensed heterocyclic compound that has an enteropeptidase inhibitory effect and is useful in the treatment or prevention of obesity, diabetes mellitus, or the like, and a medicament containing the same.

Background of Invention

Enteropeptidase is a serine protease that converts trypsinogen secreted from the pancreas after meal to trypsin. Trypsin in a state activated by enteropeptidase then activates protease precursors such as chymotrypsinogen, procarboxypeptidase, and proelastase. These activated proteases decompose dietary proteins into amino acid units. The resulting amino acids are absorbed into the small intestine. Thus, enteropeptidase inhibitors are capable of suppressing the degradation or absorption of proteins and is useful as a drug for treating obesity.

Examples of heterocyclic compounds include the following:

(1) A compound which has a trypsin inhibitory effect and is useful in the treatment or prevention of a renal disease or a disease involving trypsin, the compound being represented by the following formula:

[Formula 1]

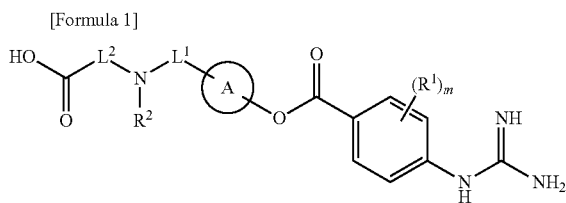

wherein
ring A represents

[Formula 2]

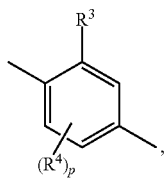

(a)

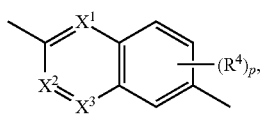

(b)

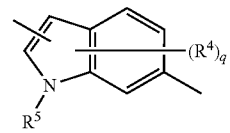

(c)

$R^1$ represents H, halogen, lower alkyl, or OH;

$R^2$ represents H, optionally substituted cycloalkyl, optionally substituted aryl, an optionally substituted aromatic heterocyclic ring, an optionally substituted nonaromatic heterocyclic ring, —C(O)-lower alkylene-optionally substituted aryl, or an optionally substituted lower alkyl;

$L^1$ represents —$Y^1$-lower alkylene-$Y^2$—, or —C(O)—N($R^6$)—;

$Y^1$ represents a bond or —C(O)—;

$Y^2$ represents a bond, —N($R^6$)—, or —C(O)—N($R^6$)—;

$L^2$ represents -(lower alkylene optionally substituted by $CO_2H$ or the like)-, —$Y^3$-cyclohexanediyl-$Y^4$—, or —$Y^3$-phenylene-$Y^4$—, and $L^2$ optionally forms optionally substituted cyclic amino together with $R^2$;

$Y^3$ represents a bond or lower alkylene;

$Y^4$ represents a bond, lower alkylene, or —C(O)—;

$R^3$ represents H, lower alkyl optionally substituted by halogen, halogen, OH, —O-lower alkyl, cycloalkyl, aryl, or the like;

$R^4$ represents lower alkyl optionally substituted by halogen, halogen, OH, —O-lower alkyl, cycloalkyl, aryl, or the like;

$R^5$ and $R^6$ each represent H or lower alkyl;

$X^1$, $X^2$, and $X^3$ each represent CH or N (except that at least one of $X^1$, $X^2$, and $X^3$ is N);

m represents an integer of 0 to 4;

p represents an integer of 0 to 3; and q represents an integer of 0 to 4

(Patent Literature 1).

(2) A compound which has a serine protease inhibitory effect and is useful in the treatment or prevention of obesity, hyperlipidemia, diabetes mellitus, diabetic complications, or metabolic syndrome, the compound being represented by the following formula:

[Formula 3]

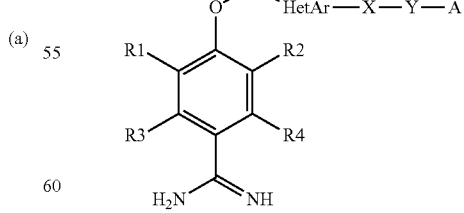

wherein

R1, R2, R3, and R4 each represent H or the like;

HetAr represents an optionally substituted heteroaromatic ring;

X represents optionally substituted lower alkylene or the like;

Y represents carbonyl or the like;

A represents

[Formula 4]

or the like; and

R6 and R7 each represent H, optionally substituted lower alkyl, or the like
(Patent Literature 2).

(3) A compound which has a serine protease inhibitory effect and is useful in the treatment or prevention of obesity, hyperlipidemia, diabetes mellitus, diabetic complications, or metabolic syndrome, the compound being represented by the following formula:

[Formula 5]

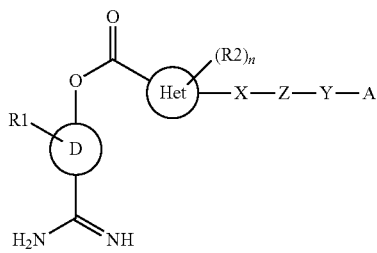

wherein

D represents a benzene ring, a naphthalene ring, or a pyridine ring;

Het represents a heterocyclic ring;

R1 represents H or the like;

R2 represents nitro, lower alkyl, or the like;

X represents optionally substituted lower alkylene;

Z represents —N(R3)- (wherein R3 represents H, optionally substituted lower alkyl, optionally substituted lower cycloalkyl, or the like);

Y represents a single bond or —(CH$_2$)p-C(R4a) (R4b)-(CH$_2$)q- (wherein R4a and R4b each represent H, lower alkyl, or aralkyl, and p and q each represents an integer of 0 to 5); and A represents —CO$_2$R6 (wherein R6 represents H or lower alkyl) or

[Formula 6]

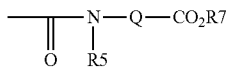

wherein Q represents optionally substituted lower alkylene, and R7 represents H or lower alkyl
(Patent Literature 3).

(4) A compound which has an enteropeptidase inhibitory effect and is useful in the treatment or prevention of a disease related to obesity or abnormal fat metabolism, the compound being represented by the following formula:

[Formula 7]

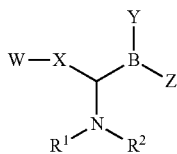

wherein

B represents boron;

W represents a nitrogen-containing functional group

[Formula 8]

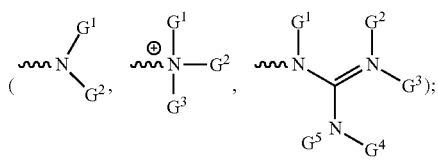

X represents a linker (CX$^1$X$^2$)p;

Y and Z each represent OH, OR (R represents alkyl), a homocyclic ring, a heterocyclic ring, or the like;

R$^1$ represents aminoacyl, acyl, or the like; and

R$^2$ represents H, alkyl, or OR (R represents H or alkyl)
(Patent Literature 4).

(5) A compound which has a serine protease inhibitory effect and is useful in the treatment or prevention of obesity, diabetes mellitus, or the like, the compound being represented by the following formula:

[Formula 9]

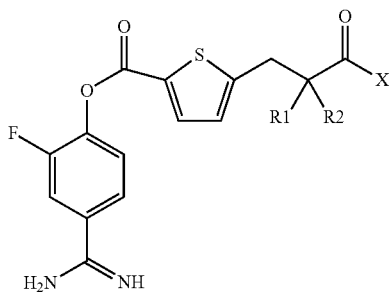

wherein

R$^1$ and R$^2$ each represent alkyl or the like; and

X represents —OR$^3$, —NR$^4$R$^5$, or the like
(Patent Literature 5).

(6) A compound which has a trypsin inhibitory effect and is useful in the treatment or prevention of a renal disease or a disease involving trypsin, the compound being represented by the following formula:

[Formula 10]

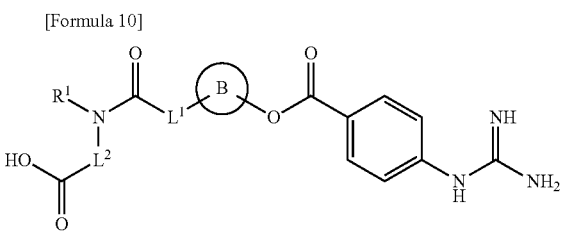

wherein
L¹ represents a bond or -lower alkylene-;
L² represents optionally substituted lower alkylene;
substituent selected from the group consisting of optionally substituted aryl, an optionally substituted aromatic heterocyclic group, and —CO₂H, or H, or R¹ optionally forms cyclic amino optionally substituted by —CO₂H, together with the nitrogen atom bonded thereto and the HO₂C-L² group on the nitrogen atom; and ring B represents naphthalenediyl, 1,2,3,4-tetrahydronaphthalenediyl, 2,3-dihydroindenediyl, benzothiophenediyl, benzofurandiyl, or 2,3-dihydrobenzofurandiyl
(Patent Literature 6).

CITATION LIST

Patent Literature

Patent Literature 1: WO2013/039187
Patent Literature 2: WO2011/071048
Patent Literature 3: WO2012/169579
Patent Literature 4: WO2009/071601
Patent Literature 5: WO2013/187533
Patent Literature 6: WO2014/142219

SUMMARY OF INVENTION

Technical Problem

An object of the present invention is to provide a condensed heterocyclic compound that has an excellent enteropeptidase inhibitory effect and is useful in the treatment or prevention of obesity, diabetes mellitus, or the like, and a medicament containing the same.

Solution to Problem

The present inventors have conducted diligent studies to attain the object and consequently completed the present invention by finding that a compound represented by the formula (I) given below has an excellent enteropeptidase inhibitory effect.
Specifically, the present invention is as follows:
[1]
A compound represented by the formula (I) or a salt thereof:

[Formula 11]

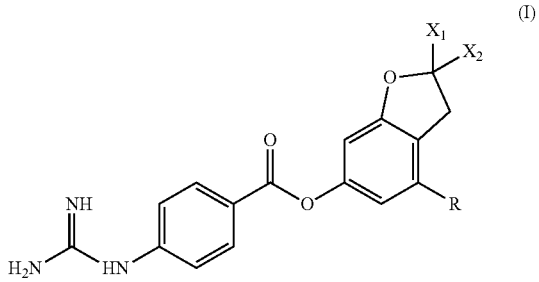

wherein
R represents

[Formula 12]

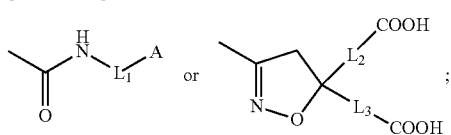

$L_1$ represents a $C_{1-6}$ alkylene group;
$L_2$ and $L_3$ are the same or different and each represent a bond or a $C_{1-6}$ alkylene group;
A represents —S(O)₂OH or —P(O)(OH)₂; and
$X_1$ and $X_2$ are the same or different and each represent H or a $C_{1-6}$ alkyl group
(hereinafter, the compound or the salt is also referred to as compound (I)).
[2]
The compound according to the above [1] or a salt thereof, wherein R is

[Formula 13]

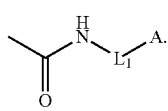

[3]
The compound according to the above [1] or [2] or a salt thereof, wherein $L_1$ is a $C_{1-3}$ alkylene group.
[4]
The compound according to any of the above [1] to [3] or a salt thereof, wherein A is —S(O)₂OH.
[5]
The compound according to the above [1] or a salt thereof, wherein R is

[Formula 14]

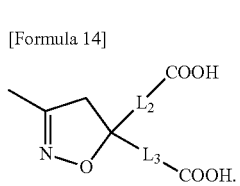

[6]
The compound according to the above [1] or [5] or a salt thereof, wherein $L_2$ is a bond, and $L_3$ is a $C_{1-3}$ alkylene group.

[7]
The compound according to any of the above [1] to [6] or a salt thereof, wherein $X_1$ and $X_2$ are the same or different and each represent H or a $C_{1-3}$ alkyl group.

[8]
The compound according to the above [1] or a salt thereof, wherein
R is

[Formula 15]

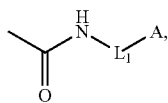

$L_1$ is a $C_{1-3}$ alkylene group, and
both of $X_1$ and $X_2$ are H.

[9]
The compound according to the above [1] or a salt thereof, wherein
R is

[Formula 16]

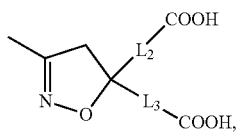

$L_2$ is a bond, $L_3$ is a $C_{1-3}$ alkylene group, and both of $X_1$ and $X_2$ are H or both of $X_1$ and $X_2$ are a $C_{1-3}$ alkyl group.

[10]
2-(((6-((4-Carbamimidamidobenzoyl)oxy)-2,3-dihydro-1-benzofuran-4-yl)carbonyl)amino)ethanesulfonic acid or a salt thereof.

[11]
((((6-((4-Carbamimidamidobenzoyl)oxy)-2,3-dihydro-1-benzofuran-4-yl)carbonyl)amino)methyl)phosphonic acid or a salt thereof.

[12]
3-(6-((4-Carbamimidamidobenzoyl)oxy)-2,3-dihydro-1-benzofuran-4-yl)-5-(carboxymethyl)-4,5-dihydro-1,2-oxazole-5-carboxylic acid or a salt thereof.

[13]
A medicament comprising a compound according to any of the above [1] to [12] or a salt thereof.

[14]
The medicament according to the above [13], wherein the medicament is an enteropeptidase inhibitor.

[15]
The medicament according to the above [13], wherein the medicament is an agent for preventing or treating obesity.

[16]
The medicament according to the above [13], wherein the medicament is an agent for preventing or treating diabetes mellitus.

[17]
A method for preventing or treating obesity or diabetes mellitus in a mammal, comprising administering an effective amount of a compound according to any of the above [1] to [12] or a salt thereof to the mammal.

[18]
A method for inhibiting enteropeptidase in a mammal, comprising administering an effective amount of a compound according to any of the above [1] to [12] or a salt thereof to the mammal.

[19]
Use of a compound according to any of the above [1] to [12] or a salt thereof for producing an agent for preventing or treating obesity or diabetes mellitus.

[20]
The compound according to any of the above [1] to [12] or a salt thereof for use in the prevention or treatment of obesity or diabetes mellitus.

Advantageous Effects of Invention

Compound (I) has an excellent enteropeptidase inhibitory effect and is useful in the treatment or prevention of obesity, diabetes mellitus, or the like.

DETAILED DESCRIPTION OF THE INVENTION

Hereinafter, the present invention will be described in detail.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),

(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and
8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkyl-phosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl)amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl)($C_{1-6}$ alkyl-carbonyl)amino group (e.g., N-acetyl-N-methylamino) and a ($C_{1-6}$ alkyl) ($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

Hereinafter, each symbol of the formula (I) will be described.

In the formula,
R represents

[Formula 17]

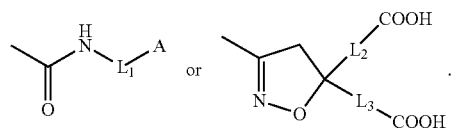

$L_1$ represents a $C_{1-6}$ alkylene group. Preferably, $L_1$ is a $C_{1-3}$ alkylene group (e.g., methylene, ethylene, and propylene).

$L_2$ and $L_3$ are the same or different and each represent a bond or a $C_{1-6}$ alkylene group. Preferably, $L_2$ is a bond, and $L_3$ is a $C_{1-6}$ alkylene group. More preferably, $L_2$ is a bond, and $L_3$ is a $C_{1-3}$ alkylene group (e.g., methylene).

A represents —S(O)$_2$OH or —P(O)(OH)$_2$. Preferably, A is —S(O)$_2$OH.

$X_1$ and $X_2$ are the same or different and each represent H or a $C_{1-6}$ alkyl group. Preferably, $X_1$ and $X_2$ are the same or different and each represent H or a $C_{1-3}$ alkyl group. More preferably, $X_1$ and $X_2$ are the same or different and each represent H or a $C_{1-3}$ alkyl group (e.g., methyl). Further preferably, both of $X_1$ and $X_2$ are H or both of $X_1$ and $X_2$ are a $C_{1-3}$ alkyl group (e.g., methyl). Particularly preferably, both of $X_1$ and $X_2$ are H.

Preferred specific examples of compound (I) include the following:

[Compound A]
Compound (I) wherein
R is

[Formula 18]

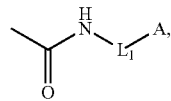

$L_1$ is a $C_{1-3}$ alkylene group (e.g., methylene, ethylene, and propylene), and
both of $X_1$ and $X_2$ are H.

[Compound B]
Compound (I) wherein
R is

[Formula 19]

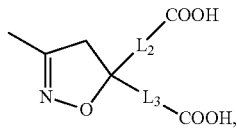

$L_2$ is a bond, $L_3$ is a $C_{1-3}$ alkylene group (e.g., methylene), and
both of $X_1$ and $X_2$ are H or both of $X_1$ and $X_2$ are a $C_{1-3}$ alkyl group (e.g., methyl).

[Compound C]
A compound of Example 1 mentioned later.
A compound of Example 4 mentioned later.
A compound of Example 6 mentioned later.

Examples of the salt of the compound represented by the formula (I) include a metal salt, ammonium salt, a salt with an organic base, a salt with an inorganic acid, a salt with an organic acid, and a salt with a basic or acidic amino acid.

Preferred examples of the metal salt include: alkali metal salts such as sodium salt and potassium salt; alkaline earth metal salts such as calcium salt, magnesium salt, and barium salt; and aluminum salt.

Preferred examples of the salt with an organic base include a salt with trimethylamine, triethylamine, pyridine, picoline, 2,6-lutidine, ethanolamine, diethanolamine, triethanolamine, cyclohexylamine, dicyclohexylamine, or N,N-dibenzylethylenediamine.

Preferred examples of the salt with an inorganic acid include a salt with hydrochloric acid, hydrobromic acid, nitric acid, sulfuric acid, or phosphoric acid.

Preferred examples of the salt with an organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, or p-toluenesulfonic acid.

Preferred examples of the salt with a basic amino acid include a salt with arginine, lysine, or ornithine. Preferred examples of the salt with an acidic amino acid include a salt with aspartic acid or glutamic acid.

Among these salts, a pharmaceutically acceptable salt is preferred.

Compound (I) may be a prodrug.

The prodrug of compound (I) refers to a compound that is converted to the compound (I) through a reaction caused by an enzyme, gastric acid, or the like under physiological conditions in vivo, i.e., a compound that is converted to the compound (I) by enzymatic oxidation, reduction, hydrolysis, etc., or a compound that is converted to the compound (I) by hydrolysis, etc., caused by gastric acid or the like.

Examples of the prodrug of compound (I) include: a compound in which amino of the compound (I) is acylated, alkylated, or phosphorylated (e.g., a compound in which amino of the compound (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, or tert-butylated); a compound in which hydroxy of the compound (I) is acylated, alkylated, phosphorylated, or borated (e.g., a compound in which hydroxy of the compound (I) is acetylated, palmitoylated, propanoylated, pivaloylated, succinylated, fumarylated, alanylated, or dimethylaminomethylcarbonylated); and a compound in which carboxy of the compound (I) is esterified or amidated (e.g., a compound in which carboxy of the compound (I) is $C_{1-6}$ alkyl-esterified, phenyl-esterified, carboxymethyl-esterified, dimethylaminomethyl-esterified, pivaloyloxymethyl-esterified, ethoxycarbonyloxyethyl-esterified, phthalidyl-esterified, (5-methyl-2-oxo-1,3-dioxolen-4-yl)methyl-esterified, cyclohexyloxycarbonylethyl-esterified, or methylamidated). Among them, a compound in which carboxy of the compound (I) is esterified with $C_{1-6}$ alkyl such as methyl, ethyl, or tert-butyl is preferably used. These compounds can be produced from the compound (I) by a method known per se in the art.

The prodrug of compound (I) may be converted to the compound (I) under physiological conditions as described in Iyakuhin No Kaihatsu (Development of Pharmaceuticals in English), Vol. 7, Molecular Design, p. 163-198, Hirokawa Shoten Ltd. (1990).

In the present specification, the prodrug may form a salt. Examples of such a salt include those listed above as the salt of the compound represented by the formula (I).

A method for producing the compound of the present invention will be described below.

A starting material or a reagent used in each step in the production method given below and the obtained compound may each form a salt. Examples of such a salt include the same as the aforementioned salt of the compound of the present invention.

When the compound obtained in each step is a free compound, this compound can be converted to a salt of interest by a method known per se in the art. On the contrary, when the compound obtained in each step is a salt, this salt can be converted to a free form or another type of salt of interest by a method known per se in the art.

The compound obtained in each step may be used in the next reaction in the form of its reaction solution or after being obtained as a crude product. Alternatively, the compound obtained in each step can be isolated and/or purified from the reaction mixture by a separation approach such as concentration, crystallization, recrystallization, distillation, solvent extraction, fractionation, or chromatography according to a routine method.

If a starting material or a reagent compound for each step is commercially available, the commercially available product can be used directly.

In the reaction of each step, the reaction time may differ depending on the reagent or the solvent used and is usually 1 minute to 48 hours, preferably 10 minutes to 8 hours, unless otherwise specified.

In the reaction of each step, the reaction temperature may differ depending on the reagent or the solvent used and is usually −78° C. to 300° C., preferably −78° C. to 150° C., unless otherwise specified.

In the reaction of each step, the pressure may differ depending on the reagent or the solvent used and is usually 1 atm to 20 atm, preferably 1 atm to 3 atm, unless otherwise specified.

In the reaction of each step, a microwave synthesis apparatus, for example, Initiator manufactured by Biotage Japan Ltd., may be used. The reaction temperature may differ depending on the reagent or the solvent used and is usually room temperature to 300° C., preferably 50° C. to 250° C., unless otherwise specified. The reaction time may differ depending on the reagent or the solvent used and is usually 1 minute to 48 hours, preferably 1 minute to 8 hours, unless otherwise specified.

In the reaction of each step, the reagent is used at 0.5 equivalents to 20 equivalents, preferably 0.8 equivalents to 5 equivalents, with respect to the substrate, unless otherwise specified. In the case of using the reagent as a catalyst, the reagent is used at 0.001 equivalents to 1 equivalent, preferably 0.01 equivalents to 0.2 equivalents, with respect to the substrate. When the reagent also serves as a reaction solvent, the reagent is used in the amount of the solvent.

In the reaction of each step, this reaction is carried out without a solvent or by dissolution or suspension in an appropriate solvent, unless otherwise specified. Specific examples of the solvent include solvents described in Examples and the following: alcohols: methanol, ethanol, tert-butyl alcohol, 2-methoxyethanol, and the like;
ethers: diethyl ether, diphenyl ether, tetrahydrofuran, 1,2-dimethoxyethane, and the like;
aromatic hydrocarbons: chlorobenzene, toluene, xylene, and the like;
saturated hydrocarbons: cyclohexane, hexane, and the like;
amides: N,N-dimethylformamide, N-methylpyrrolidone, and the like;
halogenated hydrocarbons: dichloromethane, carbon tetrachloride, and the like;
nitriles: acetonitrile and the like;
sulfoxides: dimethyl sulfoxide and the like;
aromatic organic bases: pyridine and the like;
acid anhydrides: acetic anhydride and the like;
organic acids: formic acid, acetic acid, trifluoroacetic acid, and the like;
inorganic acids: hydrochloric acid, sulfuric acid, and the like;
esters: ethyl acetate and the like;
ketones: acetone, methyl ethyl ketone, and the like; and water.

Two or more of these solvents may be used as a mixture at an appropriate ratio.

In the case of using a base in the reaction of each step, for example, the following base or a base described in Examples is used:
inorganic bases: sodium hydroxide, magnesium hydroxide, and the like;
basic salts: sodium carbonate, calcium carbonate, sodium bicarbonate, and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine, and the like;
metal alkoxides: sodium ethoxide, potassium tert-butoxide, and the like;
alkali metal hydrides: sodium hydride, and the like;
metal amides: sodium amide, lithium diisopropylamide, lithium hexamethyldisilazide, and the like; and
organic lithiums: n-butyllithium and the like.

In the case of using an acid or an acidic catalyst in the reaction of each step, for example, the following acid or acidic catalyst or an acid or an acidic catalyst described in Examples is used:
inorganic acids: hydrochloric acid, sulfuric acid, nitric acid, hydrobromic acid, phosphoric acid, and the like;
organic acids: acetic acid, trifluoroacetic acid, citric acid, p-toluenesulfonic acid, 10-camphorsulfonic acid, and the like; and Lewis acids: boron trifluoride-diethyl ether complex, zinc iodide, anhydrous aluminum chloride, anhydrous zinc chloride, anhydrous iron chloride, and the like.

The reaction of each step is carried out according to a method known per se in the art, for example, a method described in The Fifth Series of Experimental Chemistry, Vol. 13 to Vol. 19 (edited by The Chemical Society of Japan); Shin Jikken Kagaku Koza (New Experimental Chemistry in English), Vol. 14 to Vol. 15 (edited by The Chemical Society of Japan); Syntheses in the Organic Chemistry Laboratory, Revised, 2nd Ed. (L. F. Tietze, Th. Eicher, Nankodo Co., Ltd.); Organic Name Reactions; The Reaction Mechanism and Essence, Revised (Hideo Tougo, Kodansha Ltd.); Organic Syntheses Collective Volume I to VII (John Wiley & Sons, Inc.); Modern Organic Synthesis in the Laboratory: A Collection of Standard Experimental Procedures (Jie Jack Li, Oxford University Press); Comprehensive Heterocyclic Chemistry III, Vol. 1 to Vol. 14 (Elsevier Japan K K); Strategic Applications of Named Reactions in Organic Synthesis (translated by Kiyoshi Tomioka, published by Kagaku-Dojin Publishing Company, Inc.); Comprehensive Organic Transformations (VCH Publishers, Inc.) (1989), etc., or a method described in Examples, unless otherwise specified.

In each step, the protection or deprotection reaction of a functional group is carried out according to a method known per se in the art, for example, a method described in "Protective Groups in Organic Synthesis, 4th Ed." (Theodora W. Greene, Peter G. M. Wuts), Wiley-Interscience (2007); "Protecting Groups, 3rd Ed." (P. J. Kocienski), Thieme Medical Publishers (2004), etc., or a method described in Examples.

Examples of a protective group for a hydroxy group or a phenolic hydroxy group in an alcohol or the like include: ether-type protective groups such as methoxy methyl ether, benzyl ether, t-butyl dimethyl silyl ether, and tetrahydropyranyl ether; carboxylic acid ester-type protective groups such as acetic acid ester; sulfonic acid ester-type protective groups such as methanesulfonic acid ester; and carbonic acid ester-type protective groups such as t-butyl carbonate.

Examples of a protective group for a carbonyl group in an aldehyde include: acetal-type protective groups such as dimethylacetal; and cyclic acetal-type protective groups such as cyclic 1,3-dioxane.

Examples of a protective group for a carbonyl group in a ketone include: ketal-type protective groups such as dimethylketal; cyclic ketal-type protective groups such as cyclic 1,3-dioxane; oxime-type protective groups such as O-methyloxime; and hydrazone-type protective groups such as N,N-dimethylhydrazone.

Examples of a protective group for a carboxy group include: ester-type protective groups such as methyl ester; and amide-type protective groups such as N,N-dimethylamide.

Examples of a protective group for a thiol include: ether-type protective groups such as benzyl thioether; and ester-type protective groups such as thioacetic acid ester, thiocarbonate, and thiocarbamate.

Examples of a protective group for an amino group or an aromatic heterocyclic ring such as imidazole, pyrrole, or indole include: carbamate-type protective groups such as benzyl carbamate; amide-type protective groups such as acetamide; alkylamine-type protective groups such as N-triphenylmethylamine; and sulfonamide-type protective groups such as methanesulfonamide.

These protective groups can be removed by use of a method known per se in the art, for example, a method using an acid, a base, ultraviolet light, hydrazine, phenylhydrazine, sodium N-methyldithiocarbamate, tetrabutylammonium fluoride, palladium acetate, or trialkylsilyl halide (e.g., trimethylsilyl iodide and trimethylsilyl bromide), or a reduction method.

In the case of carrying out reduction reaction in each step, examples of the reducing agent used include: metal hydrides such as lithium aluminum hydride, sodium triacetoxyborohydride, sodium cyanoborohydride, diisobutyl aluminum hydride (DIBAL-H), sodium borohydride, and tetramethylammonium triacetoxyborohydride; boranes such as a borane-tetrahydrofuran complex; Raney nickel; Raney cobalt; hydrogen; and formic acid. In the case of reducing a carbon-carbon double bond or triple bond, a method using a catalyst such as palladium-carbon or a Lindlar's catalyst can be used.

In the case of carrying out oxidation reaction in each step, examples of the oxidizing agent used include: peracids such as m-chloroperbenzoic acid (MCPBA), hydrogen peroxide, and t-butyl hydroperoxide; perchlorates such as tetrabutylammonium perchlorate; chlorates such as sodium chlorate; chlorites such as sodium chlorite; periodates such as sodium periodate; high-valent iodine reagents such as iodosylbenzene; reagents having manganese, such as manganese dioxide and potassium permanganate; leads such as lead tetraacetate; reagents having chromium, such as pyridinium chlorochromate (PCC), pyridinium dichromate (PDC), and Jones reagents; halogen compounds such as N-bromosuccinimide (NBS); oxygen; ozone; a sulfur trioxide-pyridine complex; osmium tetroxide; selenium dioxide; and 2,3-dichloro-5,6-dicyano-1,4-benzoquinone (DDQ).

In the case of carrying out radical cyclization reaction in each step, examples of the radical initiator used include: azo compounds such as azobisisobutyronitrile (AIBN); water-soluble radical initiators such as 4-4'-azobis-4-cyanopentanoic acid (ACPA); triethylboron in the presence of air or oxygen; and benzoyl peroxide. Examples of the radical reaction agent used include tributylstannane, tristrimethylsilylsilane, 1,1,2,2-tetraphenyldisilane, diphenylsilane, and samarium iodide.

In the case of carrying out Wittig reaction in each step, examples of the Wittig reagent used include alkylidenephosphoranes. The alkylidenephosphoranes can be prepared by a method known per se in the art, for example, the reaction between a phosphonium salt and a strong base.

In the case of carrying out Horner-Emmons reaction in each step, examples of the reagent used include: phosphonoacetic acid esters such as methyl dimethylphosphonoacetate and ethyl diethylphosphonoacetate; and bases such as alkali metal hydrides and organic lithiums.

In the case of carrying out Friedel-Crafts reaction in each step, examples of the reagent used include a Lewis acid and an acid chloride or an alkylating agent (e.g., alkyl halides, alcohols, and olefins). Alternatively, an organic acid or an inorganic acid may be used instead of the Lewis acid, and an acid anhydride such as acetic anhydride may be used instead of the acid chloride.

In the case of carrying out aromatic nucleophilic substitution reaction in each step, a nucleophile (e.g., amines and imidazole) and a base (e.g., basic salts and organic bases) are used as reagents.

In the case of carrying out nucleophilic addition reaction using a carbanion, nucleophilic 1,4-addition reaction (Michael addition reaction) using a carbanion, or nucleophilic substitution reaction using a carbanion in each step, examples of the base used for generating the carbanion include organic lithiums, metal alkoxides, inorganic bases, and organic bases.

In the case of carrying out Grignard reaction in each step, examples of the Grignard reagent include: aryl magnesium halides such as phenyl magnesium bromide; and alkyl magnesium halides such as methyl magnesium bromide.

The Grignard reagent can be prepared by a method known per se in the art, for example, the reaction between alkyl halide or aryl halide and metal magnesium with ether or tetrahydrofuran as a solvent.

In the case of carrying out Knoevenagel condensation reaction in each step, an active methylene compound flanked by two electron-attracting groups (e.g., malonic acid, diethyl malonate, and malononitrile) and a base (e.g., organic bases, metal alkoxides, and inorganic bases) are used as reagents.

In the case of carrying out Vilsmeier-Haack reaction in each step, phosphoryl chloride and an amide derivative (e.g., N,N-dimethylformamide) are used as reagents.

In the case of carrying out azidation reaction of alcohols, alkyl halides, or sulfonic acid esters in each step, examples of the azidating agent used include diphenylphosphorylazide (DPPA), trimethylsilylazide, and sodium azide. In the case of azidating, for example, alcohols, a method using diphenylphosphorylazide and 1,8-diazabicyclo[5.4.0]undec-7-ene (DBU), a method using trimethylsilylazide and a Lewis acid, or the like can be used.

In the case of carrying out reductive amination reaction in each step, examples of the reducing agent used include sodium triacetoxyborohydride, sodium cyanoborohydride, hydrogen, and formic acid. When the substrate is an amine compound, examples of the carbonyl compound used include p-formaldehyde as well as aldehydes such as acetaldehyde, and ketones such as cyclohexanone. When the substrate is a carbonyl compound, examples of the amines used include: primary amine such as ammonia and methylamine; and secondary amine such as dimethylamine.

In the case of carrying out Mitsunobu reaction in each step, azodicarboxylic acid esters (e.g., diethyl azodicarboxylate (DEAD) and diisopropyl azodicarboxylate (DIAD)) and triphenylphosphine are used as reagents.

In the case of carrying out esterification reaction, amidation reaction, or ureation reaction in each step, examples of the reagent used include: an acyl halide form of acid chloride, acid bromide, and the like; and activated carboxylic acids such as an acid anhydride, an active ester form, and a sulfuric acid ester form. Examples of the activator for carboxylic acid include: carbodiimide condensing agents such as 1-ethyl-3-(3-dimethylaminopropyl) carbodiimide hydrochloride (WSCD); triazine condensing agents such as 4-(4,6-dimethoxy-1,3,5-triazin-2-yl)-4-methylmorpholinium chloride-n-hydrate (DMT-MM); carbonic acid ester condensing agents such as 1,1-carbonyldiimidazole (CDI); diphenylphosphorylazide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformate such as ethyl chloroformate; O-(7-azabenzotriazol-1-yl)-N,N,N',N'-tetramethyluronium hexafluorophosphate (HATU); sulfuric acid; and combinations thereof. In the case of using a carbodiimide condensing agent, an additive such as 1-hydroxybenzotriazole (HOBt), N-hydroxysuccinimide (HOSu), or dimethylaminopyridine (DMAP) may be further added for the reaction.

In the case of carrying out coupling reaction in each step, examples of the metal catalyst used include: palladium compounds such as palladium(II) acetate, tetrakis(triphenylphosphine)palladium(0), dichlorobis(triphenylphosphine) palladium(II), dichlorobis(triethylphosphine)palladium(II), tris(dibenzylideneacetone)dipalladium(0), and 1,1'-bis(diphenylphosphino)ferrocene palladium(II) chloride; nickel compounds such as tetrakis(triphenylphosphine)nickel(0); rhodium compounds such as tris(triphenylphosphine)rhodium(III) chloride; cobalt compounds; copper compounds such as copper oxide and copper(I) iodide; and platinum compounds. A base may be further added for the reaction. Examples of such a base include inorganic bases and basic salts.

In the case of carrying out thiocarbonylation reaction in each step, diphosphorus pentasulfide is typically used as a thiocarbonylating agent. A reagent having a 1,3,2,4-dithiadiphosphetane-2,4-disulfide structure such as 2,4-bis(4-methoxyphenyl-1,3,2,4-dithiadiphosphetane-2,4-disulfide (Lawesson's reagent) may be used instead of diphosphorus pentasulfide.

In the case of carrying out Wohl-Ziegler reaction in each step, examples of the halogenating agent used include N-iodosuccinimide, N-bromosuccinimide (NBS), N-chlorosuccinimide (NCS), bromine, and sulfuryl chloride. The reaction can be accelerated by the further addition of a radical initiator such as heat, light, benzoyl peroxide, or azobisisobutyronitrile for the reaction.

In the case of carrying out halogenation reaction of a hydroxy group in each step, examples of the halogenating agent used include a hydrohalic acid and an acid halide of an inorganic acid, specifically, hydrochloric acid, thionyl chloride, and phosphorus oxychloride for chlorination, and 48% hydrobromic acid for bromination. Also, a method for obtaining an alkyl halide form from an alcohol by the action of triphenylphosphine and carbon tetrachloride or carbon tetrabromide or the like may be used. Alternatively, a method for synthesizing an alkyl halide form through 2-stage reactions involving the conversion of an alcohol to sulfonic acid ester and the subsequent reaction with lithium bromide, lithium chloride, or sodium iodide may be used.

In the case of carrying out Arbuzov reaction in each step, examples of the reagent used include: alkyl halides such as ethyl bromoacetate; and phosphites such as triethyl phosphite and tri(isopropyl) phosphite.

In the case of carrying out sulfone-esterification reaction in each step, examples of the sulfonylating agent used include methanesulfonyl chloride, p-toluenesulfonyl chloride, methanesulfonic anhydride, and p-toluenesulfonic anhydride.

In the case of carrying out hydrolysis reaction in each step, an acid or a base is used as a reagent. In the case of carrying out acid hydrolysis reaction of t-butyl ester, formic acid, triethylsilane, or the like may be added in order to reductively trap a by-product t-butyl cation.

In the case of carrying out dehydration reaction in each step, examples of the dehydrating agent used include sulfuric acid, diphosphorus pentoxide, phosphorus oxychloride, N,N'-dicyclohexylcarbodiimide, alumina, and polyphosphoric acid.

Among the compounds (I), compound (6) can be produced by a method shown below from compound (1).

In the formula, $R^1$ represents a benzyl group optionally having a substituent, and the other symbols are as defined above.

[Formula 20]

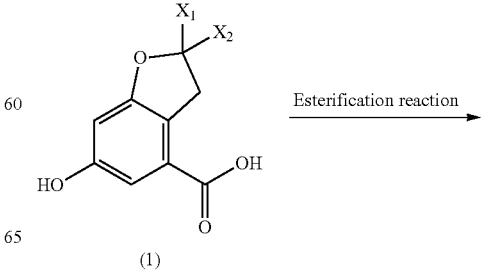

Esterification reaction

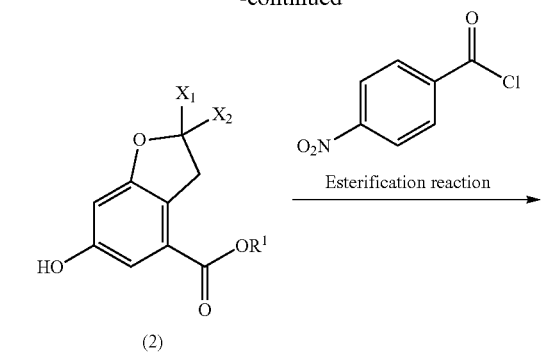
(2)
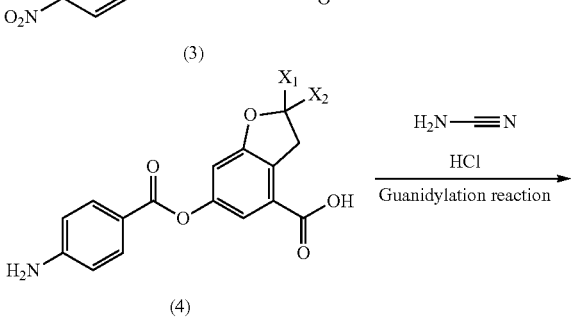
(3)
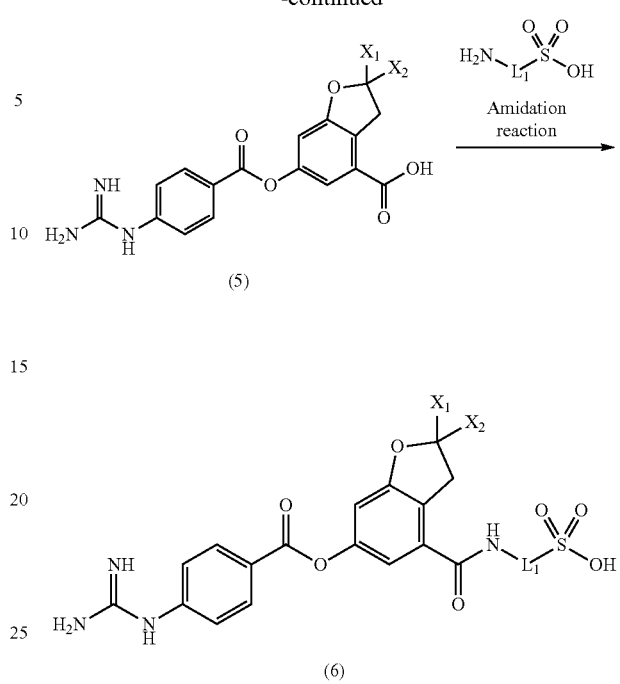
(5)
(6)
Compound (5) can be produced through the reaction of compound (4) with cyanamide under acidic conditions.
Among the compounds (I), compound (9) can be produced by a method shown below from compound (1). In the formula, $R^2$ represents a $C_{1-6}$ alkyl group, and the other symbols are as defined above.
[Formula 21]
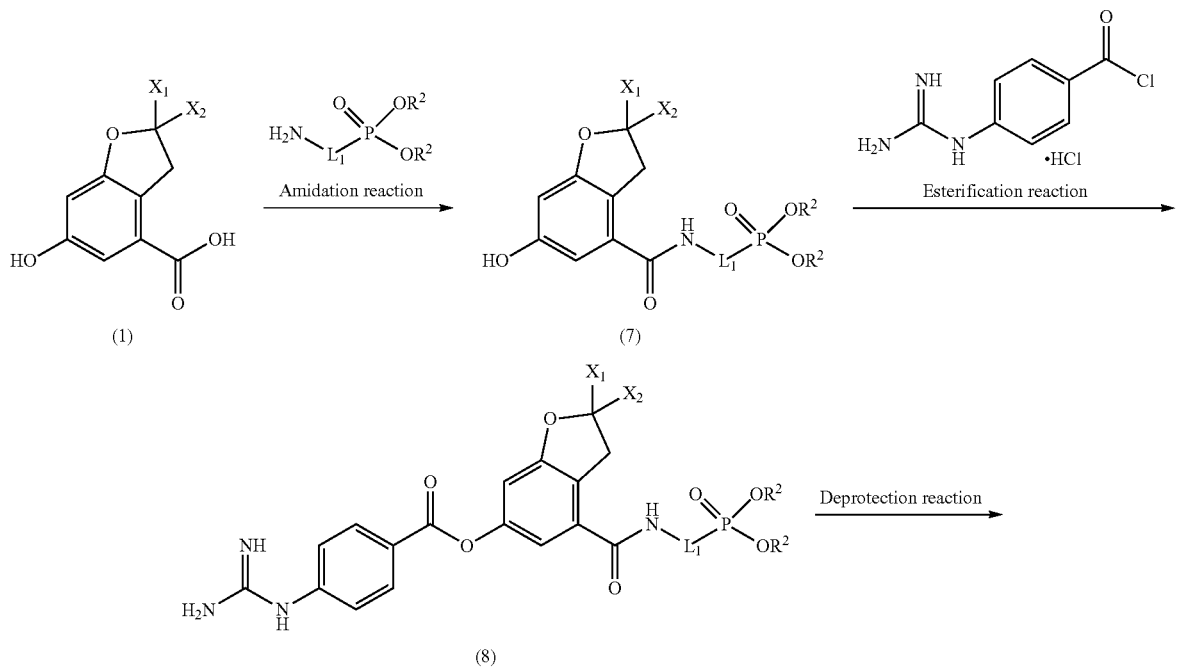

[Formula 21]
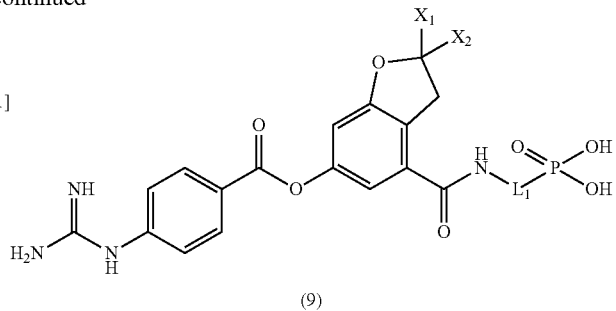
(9)
Among the compounds (I), compound (19) can be produced by a method shown below from compound (10). In the formula, $R^3$ represents a protective group for a phenolic hydroxy group, $R^4$ represents a protective group for a carboxy group, and the other symbols are as defined above.
[Formula 22]
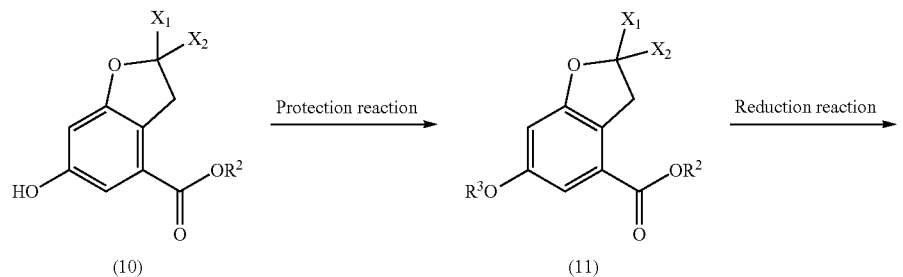
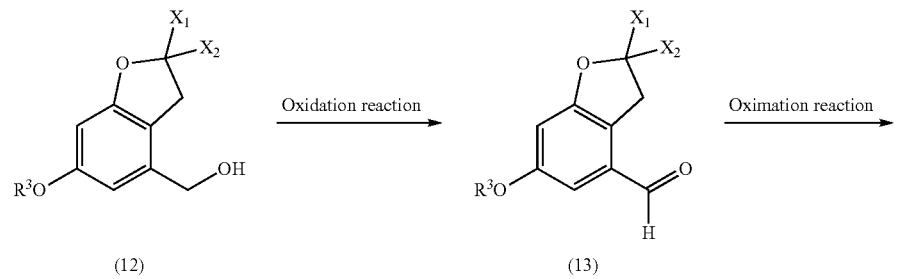
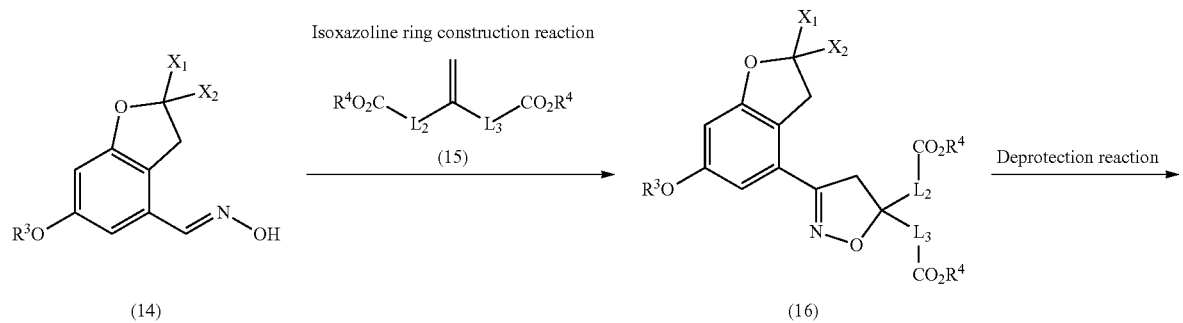

-continued

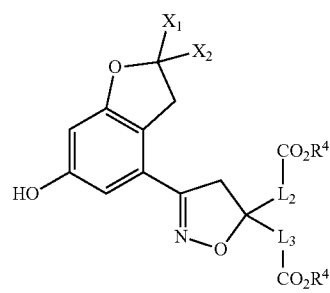
(17)

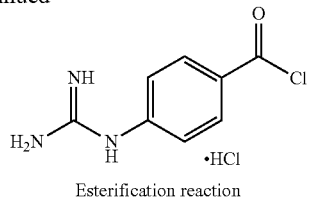
Esterification reaction →

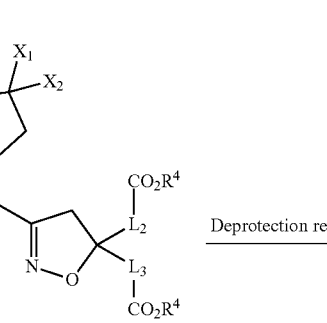
(18)

Deprotection reaction →

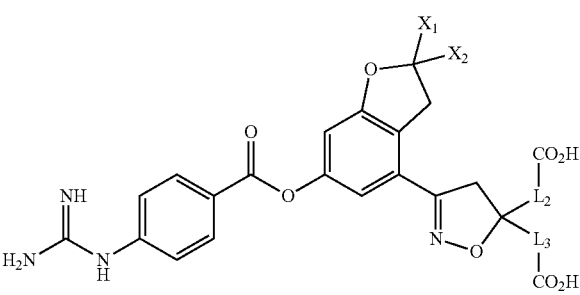
(19)

Compound (14) can be produced through the reaction of compound (13) with hydroxylamine chloride under basic conditions.

Compound (16) can be produced through the cyclization reaction of the compound (14) with compound (15) in the presence of an oxidizing agent. Examples of the oxidizing agent include sodium hypochlorite.

The compounds (1) and (10) can be produced by the following method for producing compounds (10') and (1') or a method equivalent thereto from compound (20). In the formula, the symbols are as defined above.

[Formula 23]

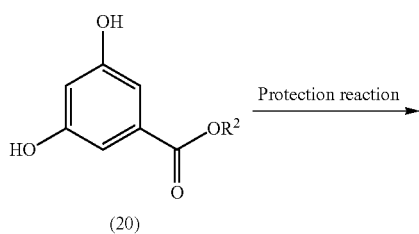
(20)

Protection reaction →

-continued

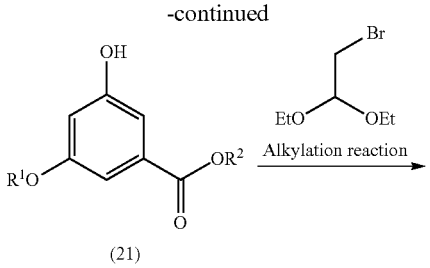
(21)

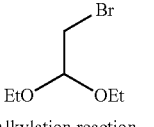

Alkylation reaction →

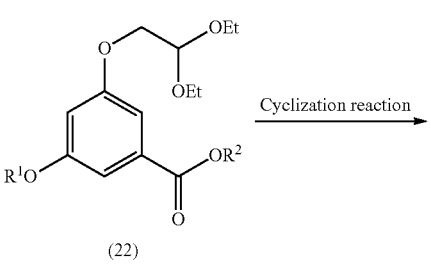
(22)

Cyclization reaction →

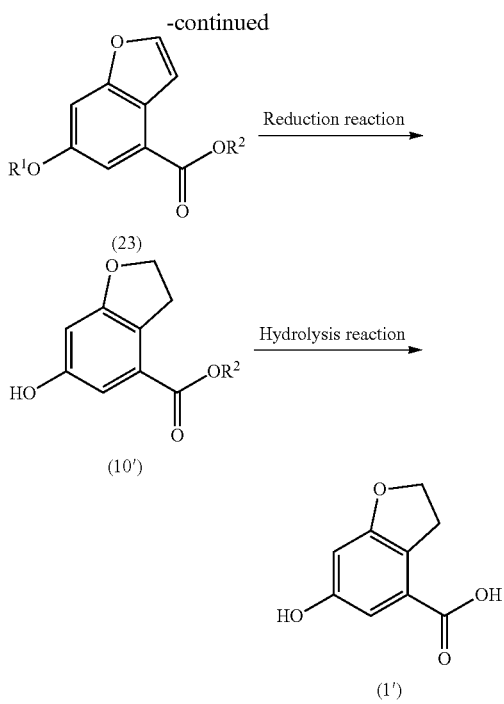

Compound (23) can be produced through the cyclization reaction of compound (22) under acidic conditions. Examples of the reactant include polyphosphoric acid.

Compound (I) may have isomers such as optical isomers, stereoisomers, positional isomers, and rotational isomers. In such a case, one of the isomers and an isomeric mixture thereof are also included in compound (I). For example, when compound (I) has optical isomers, optical isomers resolved from a racemate are also included in compound (I). These isomers can each be obtained as a single compound by a synthesis approach, a separation approach (e.g., concentration, solvent extraction, column chromatography, and recrystallization), an optical resolution approach (e.g., fractional crystallization method, chiral column method, and diastereomer method,), and the like known per se in the art.

Compound (I) may be crystals. Single crystal forms and polymorphic mixtures are both included in compound (I). The crystals can be produced by crystallizing compound (I) by the application of a crystallization method known per se in the art.

In addition, compound (I) may be a pharmaceutically acceptable cocrystal or cocrystal salt. In this context, the cocrystal or the cocrystal salt means a crystalline substance constituted by two or more unique substances that are solids at room temperature and differ in physical properties (e.g., structure, melting point, heat of melting, hygroscopicity, solubility, and stability). The cocrystal and the cocrystal salt can be produced according to a cocrystallization method known per se in the art.

In the present specification, a melting point means a melting point that is measured using, for example, a micro melting point apparatus (Yanaco model MP-500D or Buchi model B-545) or a DSC (differential scanning calorimetry) apparatus (SEIKO EXSTAR6000).

In general, melting points may vary depending on a measurement apparatus, measurement conditions, etc. In the present specification, the crystals may be crystals that exhibit a value different from the melting points described in the present specification as long as the value falls within a usual margin of error.

The crystals of the present invention are excellent in physicochemical properties (e.g., melting point, solubility, and stability) and biological properties (e.g., disposition (absorbability, distribution, metabolism, and excretion), and manifestation of efficacy) and are very useful as a medicament.

Compound (I) may be a solvate (e.g., a hydrate) or may be a non-solvate (e.g., a non-hydrate). All of them are included in compound (I).

A compound labeled with an isotope (e.g., $^3H$, $^{13}C$, $^{14}C$, $^{18}F$, $^{35}S$, and $^{125}I$) or the like is also included in compound (I).

A deuterium conversion form wherein $^1H$ is converted to $^2H(D)$ is also included in compound (I).

Compound (I) labeled or substituted with an isotope can be used as, for example, a tracer (PET tracer) for use in positron emission tomography (PET), and is useful in the fields of medical diagnosis and the like.

Compound (I) or a prodrug thereof (hereinafter, collectively referred to as the compound of the present invention) has an excellent enteropeptidase inhibitory effect, particularly, in vivo, and is useful as an enteropeptidase inhibitor.

The compound of the present invention has low toxicity (e.g., acute toxicity, chronic toxicity, genetic toxicity, reproductive toxicity, cardiac toxicity, and carcinogenicity). Thus, the compound of the present invention can be prepared into a pharmaceutical composition alone or as a mixture with a pharmacologically acceptable carrier or the like and thereby administered safely to a mammal (e.g., a mouse, a rat, a hamster, a rabbit, a cat, a dog, cattle, sheep, a monkey, and a human).

The compound of the present invention is useful as an agent for preventing or treating conditions or diseases caused by enteropeptidase.

Also, the compound of the present invention is low absorbable orally and is excellent in metabolic stability.

Specifically, the compound of the present invention can be used as an agent for preventing or treating obesity based on symptomatic obesity or simple obesity, conditions or diseases associated with obesity, eating disorder, diabetes mellitus (e.g., type 1 diabetes mellitus, type 2 diabetes mellitus, gestational diabetes mellitus, and obese diabetes mellitus), hyperlipidemia (e.g., hypertriglyceridemia, hypercholesterolemia, high LDL-cholesterolemia, low HDL-cholesterolemia, and postprandial hyperlipidemia), hypertension, cardiac failure, diabetic complications [e.g., neuropathy, nephropathy, retinopathy, diabetic cardiomyopathy, cataract, macroangiopathy, osteopenia, hyperosmolar diabetic coma, infectious disease (e.g., respiratory infection, urinary tract infection, gastrointestinal infection, dermal soft tissue infection, and inferior limb infection), diabetic gangrene, xerostomia, hypacusis, cerebrovascular disorder, and peripheral blood circulation disorder], metabolic syndrome (conditions having 3 or more selected from hypertriglycerid(TG)emia, low HDL cholesterol(HDL-C)emia, hypertension, abdominal obesity, and impaired glucose tolerance), sarcopenia, reflux esophagitis, and the like.

The compound of the present invention is particularly useful as an agent for preventing or treating obesity or an agent for preventing or treating diabetes mellitus on the basis of its enteropeptidase inhibitory effect.

Examples of the symptomatic obesity include endocrine obesity (e.g., Cushing syndrome, hypothyroidism, insulinoma, obese type II diabetes mellitus, pseudohypoparathyroidism, and hypogonadism), central obesity (e.g., hypothalamic obesity, frontal lobe syndrome, and Kleine-Levin syndrome), genetic obesity (e.g., Prader-Willi syndrome and Laurence-Moon-Biedl syndrome), and drug-induced obesity (e.g., obesity caused by steroids, phenothiazines, insulins, sulfonylurea (SU) agents, and β-blockers).

Examples of the conditions or the diseases associated with obesity include impaired glucose tolerance, diabetes mellitus (particularly, type 2 diabetes mellitus and obese diabetes mellitus), abnormal lipid metabolism (which has the same meaning as that of the hyperlipidemia mentioned above), hypertension, cardiac failure, hyperuricemia or gout, fatty liver (including non-alcoholic steato-hepatitis), coronary diseases (myocardial infarction and angina pectoris), cerebral infarction (cerebral thrombosis and transient ischemic attack), bone or joint diseases (knee osteoarthritis, hip osteoarthritis, spondylosis deformans, and lumbago), sleep apnea syndrome or Pickwick syndrome, menstruation disorder (disorder of menstrual cycle, abnormality of the amount of blood lost at menstrual period and menstrual cycle, amenorrhea, and abnormality of menstruation-related symptoms), and metabolic syndrome.

The Japan Diabetes Society reported the diagnostic criteria of diabetes mellitus in 1999.

According to this report, diabetes mellitus refers to a state that meets any of a fasting blood glucose level (glucose concentration in venous plasma) of 126 mg/dl or more, a 2-hr value (glucose concentration in venous plasma) of 200 mg/dl or more in the 75 g oral glucose tolerance test (75 g OGTT), and a casual blood glucose level (glucose concentration in venous plasma) of 200 mg/dl or more. Also, a state that does not apply to the diabetes mellitus described above, and is not a state exhibiting "a fasting blood glucose level (glucose concentration in venous plasma) of less than 110 mg/dl or a 2-hr value (glucose concentration in venous plasma) of less than 140 mg/dl in the 75 g oral glucose tolerance test (75 g OGTT)" (normal type) is called "borderline type".

Also, the diagnostic criteria of diabetes mellitus were reported in 1997 by ADA (American Diabetes Association) and in 1998 by WHO (World Health Organization).

According to these reports, diabetes mellitus refers to a state that exhibits a fasting blood glucose level (glucose concentration in venous plasma) of 126 mg/dl or more and a 2-hr value (glucose concentration in venous plasma) of 200 mg/dl or more in the 75 g oral glucose tolerance test According to the reports of ADA and WHO, impaired glucose tolerance (IGT) refers to a state that exhibits a fasting blood glucose level (glucose concentration in venous plasma) of less than 126 mg/dl and a 2-hr value (glucose concentration in venous plasma) of 140 mg/dl or more and less than 200 mg/dl in the 75 g oral glucose tolerance test. According to the report of ADA, a state exhibiting a fasting blood glucose level (glucose concentration in venous plasma) of 110 mg/dl or more and less than 126 mg/dl is called IFG (impaired fasting glucose). On the other hand, according to the report of WHO, an IFG (impaired fasting glucose) state exhibiting a 2-hr value (glucose concentration in venous plasma) less than 140 mg/dl in the 75 g oral glucose tolerance test is called IFG (impaired fasting glycemia).

The compound of the present invention is also used as an agent for preventing or treating diabetes mellitus, borderline type, impaired glucose tolerance, IFG (impaired fasting glucose), and IFG (impaired fasting glycemia) determined according to the diagnostic criteria described above. In addition, the compound of the present invention can also prevent the progression of borderline type, impaired glucose tolerance, IFG (impaired fasting glucose), or IFG (impaired fasting glycemia) into diabetes mellitus.

The compound of the present invention has an effect of suppressing body weight gain and as such, can be used as an agent suppressing body weight gain in a mammal. The mammal to which the compound of the present invention is to be applied can be any mammal desired to avoid body weight gain and may be a mammal genetically having a risk of body weight gain or may be a mammal affected by a lifestyle-related disease such as diabetes mellitus, hypertension, and/or hyperlipidemia, etc. The body weight gain may be caused by excessive dietary intake or nutritionally unbalanced diet or may be derived from concomitant drugs (e.g., insulin sensitizers having a PPAR-gamma agonist-like effect, such as troglitazone, rosiglitazone, englitazone, ciglitazone, and pioglitazone). Also, the body weight gain may be body weight gain before reaching obesity or may be body weight gain in an obesity patient. In this context, the obesity is defined as having BMI (body mass index: Body weight (kg)/[Height (m)]$^2$) of 25 or more (according to the criteria of the Japan Society for the Study of Obesity (JASSO)) for Japanese or having BMI of 30 or more (according to the criteria of WHO) for Westerners.

The compound of the present invention is also useful as an agent for preventing or treating metabolic syndrome. The incidence of cardiovascular disease is significantly high in metabolic syndrome patients, compared with patients with a single lifestyle-related disease. Therefore, the prevention or treatment of metabolic syndrome is exceedingly important for preventing cardiovascular disease.

The diagnostic criteria of metabolic syndrome were announced by WHO in 1999 and by NCEP in 2001. According to the diagnostic criteria of WHO, an individual having hyperinsulinemia or abnormal glucose tolerance as a requirement and two or more of visceral obesity, dyslipidemia (high TG or low HDL), and hypertension is diagnosed as having metabolic syndrome (World Health Organization: Definition, Diagnosis and Classification of Diabetes Mellitus and Its Complications. Part I: Diagnosis and Classification of Diabetes Mellitus, World Health Organization, Geneva, 1999). According to the diagnostic criteria of the Adult Treatment Panel III of the National Cholesterol Education Program (guideline of ischemic heart disease) in USA, an individual having three or more of visceral obesity, hypertriglyceridemia, low HDL-cholesterolemia, hypertension, and abnormal glucose tolerance is diagnosed as having metabolic syndrome (National Cholesterol Education Program: Executive Summary of the Third Report of National Cholesterol Education Program (NCEP) Expert Panel on Detection, Evaluation, and Treatment of High Blood Cholesterol in Adults (Adults Treatment Panel III). The Journal of the American Medical Association, Vol. 285, 2486-2497, 2001).

The compound of the present invention can also be used as an agent for preventing or treating, for example, osteoporosis, cachexia (e.g., cancerous cachexia, tuberculous cachexia, diabetic cachexia, cachexia associated with blood disease, cachexia associated with endocrine disease, cachexia associated with infectious disease, or cachexia caused by acquired immunodeficiency syndrome), fatty liver, polycystic ovary syndrome, renal disease (e.g., diabetic nephropathy, glomerulonephritis, glomerulosclerosis, nephrotic syndrome, hypertensive nephrosclerosis, and end-stage renal disease), muscular dystrophy, myocardial infarction, angina pectoris, cerebrovascular disorder (e.g., cerebral infarction and stroke), Alzheimer's disease, Parkinson's disease, anxiety disorder, dementia, insulin resistant syndrome, syndrome X, hyperinsulinemia, paresthesia caused by hyperinsulinemia, acute or chronic diarrhea, inflammatory disease (e.g., chronic rheumatoid arthritis, spondylitis deformans, arthritis deformans, lumbago, gout, post-operational or post-traumatic inflammation, bloating, neuralgia, laryngopharyngitis, cystitis, hepatitis (including non-alcoholic steatohepatitis), pneumonia, pancreatitis, enteritis, inflammatory bowel disease (including inflammatory large bowel disease), colitis ulcerosa, and gastric mucosal injury (including gastric mucosal injury caused by aspirin)), small intestinal mucosal injury, malabsorption, testicular dysfunction, visceral obesity syndrome, and sarcopenia.

The compound of the present invention can also be used as an agent for preventing or treating various cancers (particularly, breast cancer (e.g., invasive ductal breast cancer, noninvasive ductal breast cancer, and inflammatory breast cancer), prostate cancer (e.g., hormone-dependent prostate cancer and hormone-independent prostate cancer), pancreatic cancer (e.g., ductal pancreatic cancer), gastric cancer (e.g., papillary adenocarcinoma, mucous adenocarcinoma, and adenosquamous carcinoma), lung cancer (e.g., non-small cell lung cancer, small-cell lung cancer, and malignant mesothelioma), colon cancer (e.g., gastrointestinal stromal tumor), rectal cancer (e.g., gastrointestinal stromal tumor), colorectal cancer (e.g., familial colorectal cancer, hereditary non-polyposis colorectal cancer, and gastrointestinal stromal tumor), small intestinal cancer (e.g., non-Hodgkin's lymphoma and gastrointestinal stromal tumor), esophageal cancer, duodenal cancer, tongue cancer, pharyngeal cancer (e.g., nasopharyngeal cancer, oropharynx cancer, and hypopharyngeal cancer), salivary gland cancer, brain tumor (e.g., pineal astrocytoma, pilocytic astrocytoma, diffuse astrocytoma, and anaplastic astrocytoma), neurilemmoma, liver cancer (e.g., primary liver cancer and extrahepatic bile duct cancer), renal cancer (e.g., renal cell cancer and transitional cell cancer of the renal pelvis and ureter), bile duct cancer, endometrial cancer, uterine cervical cancer, ovarian cancer (e.g., epithelial ovarian cancer, extragonadal germ cell tumor, ovarian germ cell tumor, and ovarian tumor of low malignant potential), bladder cancer, urethral cancer, skin cancer (e.g., intraocular (ocular) melanoma and Merkel cell carcinoma), hemangioma, malignant lymphoma, malignant melanoma, thyroid cancer (e.g., medullary thyroid cancer), parathyroid cancer, nasal cavity cancer, sinus cancer, bone tumor (e.g., osteosarcoma, Ewing tumor, uterine sarcoma, and soft tissue sarcoma), angiofibroma, sarcoma of the retina, penis cancer, testicular tumor, pediatric solid tumor (e.g., Wilms' tumor and childhood kidney tumor), Kaposi's sarcoma, Kaposi's sarcoma caused by AIDS, tumor of maxillary sinus, fibrous histiocytoma, leiomyosarcoma, rhabdomyosarcoma, leukemia (e.g., acute myeloid leukemia and acute lymphoblastic leukemia), etc.).

The compound of the present invention can also be used for the secondary prevention or suppression of progression of various diseases described above (e.g., cardiovascular events such as myocardial infarction).

The compounds of Reference Examples 1 and 2 can be used in the same way as in the compound of the present invention.

A medicament comprising the compound of the present invention can be obtained using the compound of the present invention alone or as a mixture with a pharmacologically acceptable carrier according to a method known per se in the art (e.g., a method described in the Japanese Pharmacopoeia) as a method for producing pharmaceutical preparations, and safely administered orally or parenterally (e.g., administered intravenously, intramuscularly, subcutaneously, into an organ, into a nasal cavity, intracutaneously, through ocular instillation, intracerebrally, rectally, vaginally, intraperitoneally, to the inside of tumor, or to the proximity of tumor, and administered directly to a lesion) to a mammal as, for example, tablets (including sugar-coated tablets, film-coated tablets, sublingual tablets, orally disintegrating tablets, buccal tablets, and the like), pills, powders, granules, capsules (including soft capsules and microcapsules), troches, syrups, solutions, emulsions, suspensions, controlled release preparations (e.g., rapid release preparations, sustained-release preparations, and sustained-release microcapsules), aerosols, films, (e.g., orally disintegrating films, and patch films for application to the oral mucosa), injections (e.g., subcutaneous injections, intravenous injections, intramuscular injections, and intraperitoneal injections), transfusions, dermal preparations, ointments, lotions, patches, suppositories (e.g., rectal suppositories and vaginal suppositories), pellets, nasal preparations, pulmonary preparations (inhalants), or eye drops.

For the production of an oral preparation, the preparation may be coated, if necessary, for the purpose of taste masking, enteric properties, or durability.

Examples of the coating base for use in coating include sugar coating bases, aqueous film coating bases, enteric film coating bases, and sustained-release film coating bases.

Saccharose is used as the sugar coating base. Alternatively, one sugar coating base or two or more sugar coating bases in combination selected from talc, precipitated calcium carbonate, gelatin, gum arabic, pullulan, carnauba wax, and the like may be used.

Examples of the aqueous film coating base include: cellulose polymers such as hydroxypropylcellulose, hydroxypropylmethylcellulose, hydroxyethylcellulose, and methylhydroxyethylcellulose; synthetic polymers such as polyvinylacetal diethylaminoacetate, aminoalkyl methacrylate copolymer E [Eudragit E (trade name)], and polyvinylpyrrolidone; and polysaccharides such as pullulan.

Examples of the enteric film coating base include: cellulose polymers such as hydroxypropylmethylcellulose phthalate, hydroxypropylmethylcellulose acetate succinate, carboxymethylethylcellulose, and cellulose acetate phthalate; acrylic acid polymers such as methacrylic acid copolymer L [Eudragit L (trade name)], methacrylic acid copolymer LD [Eudragit L-30D55 (trade name)], and methacrylic acid copolymer S [Eudragit S (trade name)]; and naturally occurring substances such as shellac.

Examples of the sustained-release film coating base include: cellulose polymers such as ethyl cellulose; and acrylic acid polymers such as aminoalkyl methacrylate copolymer RS [Eudragit RS (trade name)] and an ethyl acrylate-methyl methacrylate copolymer suspension [Eudragit NE (trade name)].

The coating bases described above may be used as a mixture of two or more thereof at an appropriate ratio.

For coating, for example, a light shielding agent such as titanium oxide or red ferric oxide may be used.

The content of the compound of the present invention in the pharmaceutical preparation is approximately 0.01 to approximately 100% by weight of the whole preparation. The dose of the present invention differs depending on a recipient, an administration route, a disease, symptoms, etc. For example, when the compound of the present invention is obesity or orally administered to a diabetes mellitus patient (body weight: approximately 60 kg), the daily dose is approximately 0.01 to approximately 30 mg/kg body weight, preferably approximately 0.1 to approximately 20 mg/kg body weight, more preferably approximately 1 to approximately 20 mg/kg body weight, of the active ingredient [compound of the present invention]. This dose can be administered once a day or in several divided portions per day (e.g., in one to three potions per day).

Examples of the pharmacologically acceptable carrier described above include various organic or inorganic carrier materials routinely used as preparation materials. Examples thereof include: excipients, lubricants, binding agents, and disintegrants for solid preparations; and solvents, solubilizing agents, suspending agents, tonicity agents, buffering agents, and soothing agents for liquid preparations. If necessary, ordinary additives such as a preservative, an antioxidant, a colorant, a sweetening agent, an adsorbent, and a wetting agent can also be further used.

Examples of the excipient include lactose, saccharose, D-mannitol, starch, corn starch, crystalline cellulose, and light anhydrous silicic acid.

Examples of the lubricant include magnesium stearate, calcium stearate, talc, and colloidal silica.

Examples of the binding agent include crystalline cellulose, saccharose, D-mannitol, dextrin, hydroxypropylcellulose, hydroxypropylmethylcellulose, polyvinylpyrrolidone, starch, sucrose, gelatin, methylcellulose, and carboxymethylcellulose sodium.

Examples of the disintegrant include starch, carboxymethylcellulose, carboxymethylcellulose calcium, carboxymethyl starch sodium, and L-hydroxypropylcellulose.

Examples of the solvent include injectable water, alcohol, propylene glycol, Macrogol, sesame oil, corn oil, and olive oil.

Examples of the solubilizing agent include polyethylene glycol, propylene glycol, D-mannitol, benzyl benzoate, ethanol, trisaminomethane, cholesterol, triethanolamine, sodium carbonate, and sodium citrate.

Examples of the suspending agent include: surfactants such as stearyl triethanolamine, sodium lauryl sulfate, laurylaminopropionic acid, lecithin, benzalkonium chloride, benzethonium chloride, and glycerin monostearate; and hydrophilic polymers such as polyvinyl alcohol, polyvinylpyrrolidone, carboxymethylcellulose sodium, methylcellulose, hydroxymethylcellulose, hydroxyethylcellulose, and hydroxypropylcellulose.

Examples of the tonicity agent include glucose, D-sorbitol, sodium chloride, glycerin, and D-mannitol.

Examples of the buffering agent include buffer solutions of phosphate, acetate, carbonate, citrate, and the like.

Examples of the soothing agent include benzyl alcohol.

Examples of the preservative include p-hydroxybenzoic acid esters, chlorobutanol, benzyl alcohol, phenethyl alcohol, dehydroacetic acid, and sorbic acid.

Examples of the antioxidant include sulfites, ascorbic acid, and α-tocopherol.

Examples of the colorant include water-soluble food tar dyes (e.g., food dyes such as Food Red No. 2 and No. 3, Food Yellow No. 4 and No. 5, and Food Blue No. 1 and No. 2), water-insoluble lake dyes (e.g., aluminum salts of the water-soluble food tar dyes described above), and natural dyes (e.g., beta-carotene, chlorophyll, and ferric oxide red).

Examples of the sweetening agent include saccharin sodium, dipotassium glycyrrhizinate, aspartame, and stevia.

The compound of the present invention can be used in combination with a drug other than the compound of the present invention.

Examples of the drug (hereinafter, also referred to as a concomitant drug) that may be used in combination with the compound of the present invention include anti-obesity agents, agents for treating diabetes mellitus, agents for treating diabetic complications, agents for treating hyperlipidemia, antihypertensive agents, diuretics, chemotherapeutic agents, immunotherapeutic agents, anti-inflammatory drugs, antithrombotic agents, agents for treating osteoporosis, vitamins, antidementia drugs, drugs for the amelioration of erectile dysfunction, drugs for treating pollakiuria or urinary incontinence, and for treating difficulty of urination. Specific examples thereof include the following.

Examples of the anti-obesity agent include monoamine uptake inhibitors (e.g., phentermine, sibutramine, mazindol, fluoxetine, and tesofensine), serotonin 2C receptor agonists (e.g., lorcaserin), serotonin 6 receptor antagonists, histamine H3 receptor modulators, GABA modulators (e.g., topiramate), neuropeptide Y antagonists (e.g., velneperit), cannabinoid receptor antagonists (e.g., rimonabant and taranabant), ghrelin antagonists, ghrelin receptor antagonists, ghrelinacylation enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017), pancreatic lipase inhibitors (e.g., orlistat and cetilistat), β3 agonists (e.g., N-5984), diacylglycerol acyltransferase 1 (DGAT1) inhibitors, acetyl-CoA carboxylase (ACC) inhibitors, stearoyl-CoA desaturated enzyme inhibitors, microsomal triglyceride transfer protein inhibitors (e.g., R-256918), Na-glucose cotransporter inhibitors (e.g., JNJ-28431754 and remogliflozin), NFκ inhibitors (e.g., HE-3286), PPAR agonists (e.g., GFT-505 and DRF-11605), phosphotyrosine phosphatase inhibitors (e.g., sodium vanadate and trodusquemine), GPR119 agonists (e.g., PSN821, MBX-2982, and APD597), glucokinase activators (e.g., AZD-1656), leptin, leptin derivatives (e.g., metreleptin), CNTF (ciliary neurotrophic factor), BDNF (brain-derived neurotrophic factor), cholecystokinin agonists, glucagon-like peptide-1 (GLP-1) preparations (e.g., animal GLP-1 preparations extracted from the bovine or swine pancreas; human GLP-1 preparations genetically synthesized by using *Escherichia. coli* or yeast; fragments or derivatives of GLP-1 (e.g., exenatide and liraglutide)), amylin preparations (e.g., pramlintide and AC-2307), neuropeptide Y agonists (e.g., PYY3-36, derivatives of PYY3-36, obinepitide, TM-30339, and TM-30335), oxyntomodulin preparations: FGF21 preparations (e.g., animal FGF21 preparations extracted from the bovine or swine pancreas; human FGF21 preparations genetically synthesized using *Escherichia coli* or yeast; and fragments or derivatives of FGF21), and anorexigenic agents (e.g., P-57).

Examples of the agent for treating diabetes mellitus include insulin preparations (e.g., animal insulin preparations extracted from the bovine or swine pancreas; human insulin preparations genetically synthesized using *Escherichia coli* or yeast; zinc insulin; protamine zinc insulin; fragments or derivatives of insulin (e.g., INS-1), and oral insulin preparations), insulin sensitizers (e.g., pioglitazone or a salt thereof (preferably, hydrochloride), rosiglitazone or a salt thereof (preferably, maleate), metaglidasen, AMG-131, balaglitazone, MBX-2044, rivoglitazone, aleglitazar, chiglitazar, lobeglitazone, PLX-204, PN-2034, GFT-505, THR-0921, and compounds described in WO2007/013694, WO2007/018314, WO2008/093639, or WO2008/099794), α-glucosidase inhibitors (e.g., voglibose, acarbose, miglitol, and emiglitate), biguanides (e.g., metformin, buformin, and their salts (e.g., hydrochloride, fumarate, and succinate)), insulin secretagogues (e.g., sulfonylurea (e.g., tolbutamide, glibenclamide, gliclazide, chlorpropamide, tolazamide, acetohexamide, glycopyramide, glimepiride, glipizide, and glybuzole), repaglinide, nateglinide, mitiglinide, or calcium salt hydrate thereof), dipeptidyl peptidase IV inhibitors (e.g., alogliptin or a salt thereof (preferably, benzoate), trelagliptin or a salt thereof (preferably, succinate), Vildagliptin, Sitagliptin, saxagliptin, BI1356, GRC8200, MP-513, PF-00734200, PHX1149, SK-0403, ALS2-0426, TA-6666, TS-021, KRP-104, β3 agonists (e.g., N-5984), GPR40 agonists (e.g., fasiglifam and compounds described in WO2004/041266, WO2004/106276, WO2005/063729, WO2005/063725, WO2005/087710, WO2005/095338, WO2007/013689, or WO2008/001931), GLP-1 receptor agonists (e.g., GLP-1, GLP-1 MR preparations, liraglutide, exenatide, AVE-0010, BIM-51077, Aib(8,35)hGLP-1(7,37)NH$_2$, CJC-1131, and albiglutide), amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists, and FBPase inhibitors), SGLT2 (sodium-glucose cotransporter 2) inhibitors (e.g., dapagliflozin, AVE2268, TS-033, YM543, TA-7284, remogliflozin, and ASP1941), SGLT1 inhibitors, 11β-hydroxysteroid dehydrogenase inhibitors (e.g., BVT-3498 and INCB-13739), adiponectin or agonists thereof, IKK inhibitors (e.g., AS-2868), leptin resistance improving drugs, somatostatin receptor agonists, glucokinase activators (e.g., piragliatin, AZD1656, AZD6370, TTP-355, and compounds described in WO2006/112549, WO2007/028135, WO2008/047821, WO2008/050821, WO2008/136428, or WO2008/156757), GIP (glucose-dependent insulinotropic peptide), GPR119 agonists (e.g. PSN821, MBX-2982, and APD597), FGF21, and FGF analogs.

Examples of the agent for treating diabetic complications include aldose reductase inhibitors (e.g., tolrestat, epalrestat, zopolrestat, fidarestat, CT-112, ranirestat (AS-3201), and lidorestat), neurotrophic factor and increasing agents thereof (e.g., NGF, NT-3, BDNF, neurotrophic production or secretion promoting agents described in WO01/14372 (e.g., 4-(4-chlorophenyl)-2-(2-methyl-1-imidazolyl)-5-[3-(2-methylphenoxy)propyl]oxazole), and compounds described in WO2004/039365), PKC inhibitors (e.g., ruboxistaurin mesylate), AGE inhibitors (e.g., ALT946, N-phenacylthiazolium bromide (ALT766), EXO-226, Pyridorin, and pyridoxamine), GABA receptor agonists (e.g., gabapentin and pregabalin), serotonin and noradrenalin reuptake inhibitors (e.g., duloxetine), sodium channel inhibitors (e.g., lacosamide), active oxygen scavengers (e.g., thioctic acid), cerebral vasodilators (e.g., tiapuride and mexiletine), somatostatin receptor agonists (e.g., BIM23190), and apoptosis signal regulating kinase-1 (ASK-1) inhibitors.

Examples of the agent for treating hyperlipidemia include HMG-CoA reductase inhibitors (e.g., pravastatin, simvastatin, lovastatin, atorvastatin, fluvastatin, rosuvastatin, pitavastatin, and their salts (e.g., sodium salt and calcium salt)), squalene synthase inhibitors (e.g., compounds described in WO97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidin-4-acetic acid), fibrate compounds (e.g., bezafibrate, clofibrate, simfibrate, and clinofibrate), anion exchange resin (e.g., colestyramine), probucol, nicotinic acid drugs (e.g., nicomol, niceritrol, and Niaspan), ethyl icosapentate, phytosterol (e.g., soysterol and γ-oryzanol)), cholesterol absorption inhibitors (e.g., zechia), CETP inhibitors (e.g., dalcetrapib and anacetrapib), and ω-3 fatty acid preparations (e.g., ω-3-fatty acid ethyl esters 90).

Examples of the antihypertensive agent include angiotensin converting enzyme inhibitors (e.g., captopril, enalapril, and delapril), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, and azilsartan medoxomil), calcium antagonists (e.g., manidipine, nifedipine, amlodipine, efonidipine, nicardipine, amlodipine, and cilnidipine), β blockers (e.g., metoprolol, atenolol, propranolol, carvedilol, and pindolol), and clonidine.

Examples of the diuretic include xanthine derivatives (e.g., theobromine sodium salicylate, and theobromine calcium salicylate), thiazide preparations (e.g., ethiazide, cyclopenthiazide, trichloromethiazide, hydrochlorothiazide, hydroflumethiazide, benzylhydrochlorothiazide, penfluthiazide, poly 5 thiazide, and methyclothiazide), antialdosterone preparations (e.g., spironolactone and triamterene), carbonic anhydrase inhibitors (e.g., acetazolamide), chlorobenzenesulfonamide agents (e.g., chlortalidone, mefruside, and indapamide), azosemide, isosorbide, ethacrynic acid, piretanide, bumetanide, and furosemide.

Examples of the chemotherapeutic agent include alkylating agents (e.g., cyclophosphamide and ifosfamide), antimetabolites (e.g., methotrexate and 5-fluorouracil), anticancer antibiotics (e.g., mitomycin and adriamycin), plant-derived anticancer agents (e.g., vincristine, vindesine, and Taxol), cisplatin, carboplatin, and etoposide. Among others, a 5-fluorouracil derivative furtulon or neofurtulon is preferred.

Examples of the immunotherapeutic agent include microbial or bacterial components (e.g., muramyl dipeptide derivatives and Picibanil), polysaccharides having immunoenhancing activity (e.g., lentinan, sizofiran, and Krestin), cytokines obtained by genetic engineering approaches (e.g., interferon and interleukin (IL)), and colony-stimulating factors (e.g., granulocyte colony-stimulating factor, and erythropoietin). Among others, interleukins such as IL-1, IL-2, and IL-12 are preferred.

Examples of the anti-inflammatory drug include non-steroidal anti-inflammatory drugs such as aspirin, acetaminophen, and indomethacin.

Examples of the antithrombotic agent include heparin (e.g., heparin sodium, heparin calcium, enoxaparin sodium, and dalteparin sodium), warfarin (e.g., warfarin potassium), anti-thrombin drugs (e.g., argatroban and dabigatran), FXa inhibitors (e.g., rivaroxaban, apixaban, edoxaban, YM150, and compounds described in WO02/06234, WO2004/048363, WO2005/030740, WO2005/058823, or WO2005/113504), thrombolytic agents (e.g., urokinase, tisokinase, alteplase, nateplase, monteplase, and pamiteplase), and platelet aggregation inhibitors (e.g., ticlopidine hydrochloride, clopidogrel, prasugrel, E5555, SHC530348, cilostazol, ethyl icosapentate, beraprost sodium, and sarpogrelate hydrochloride).

Examples of the agent for treating osteoporosis include alfacalcidol, calcitriol, elcatonin, calcitonin salmon, estriol, ipriflavone, pamidronate disodium, alendronate sodium hydrate, incadronate disodium, and risedronate disodium.

Examples of the vitamin include vitamin $B_1$ and vitamin $B_{12}$.

Examples of the antidementia drug include tacrine, donepezil, rivastigmine, and galantamine.

Examples of the drug for the amelioration of erectile dysfunction include apomorphine and sildenafil citrate.

Examples of the drug for treating pollakiuria or urinary incontinence include flavoxate hydrochloride, oxybutynin hydrochloride, and propiverine hydrochloride.

Examples of the agent for treating difficulty of urination include acetylcholine esterase inhibitors (e.g., distigmine).

A drug confirmed to have a cachexia-ameliorating effect either in animal models or clinically, i.e., a cyclooxygenase inhibitor (e.g., indomethacin), a progesterone derivative (e.g., megestrol acetate), glucocorticoid (e.g., dexamethasone), a metoclopramide drug, a tetrahydrocannabinol drug, an agent improving fat metabolism (e.g., eicosapentaenoic acid), growth hormone, IGF-1, or an antibody against a cachexia-inducing factor TNF-α, LIF, IL-6 or oncostatin M, or the like can also be used in combination with the compound of the present invention.

Alternatively, a glycation inhibitor (e.g., ALT-711), a nerve regeneration-promoting drug (e.g., Y-128, VX853, and prosaptide), an antidepressant (e.g., desipramine, amitriptyline, and imipramine), an antiepileptic drug (e.g., lamotrigine, Trileptal, Keppra, Zonegran, Pregabalin, Harkoseride, and carbamazepine), an antiarrhythmic drug (e.g., mexiletine), an acetylcholine receptor ligand (e.g., ABT-594), an endothelin receptor antagonist (e.g., ABT-627), a monoamine uptake inhibitor (e.g., tramadol), a narcotic analgesic (e.g., morphine), a GABA receptor agonist (e.g., gabapentin and MR preparations of gabapentin), an α2 receptor agonist (e.g., clonidine), a local analgesic (e.g., capsaicin), an antianxiety drug (e.g., benzothiazepine), a phosphodiesterase inhibitor (e.g., sildenafil), a dopamine receptor agonist (e.g., apomorphine), midazolam, ketoconazole, or the like can also be used in combination with the compound of the present invention.

In the case of using the compound of the present invention and a concomitant drug in combination, the respective amounts of the drugs can be reduced within safe ranges in consideration of the adverse reactions of the drugs. In addition, the dosage of the concomitant drug can be reduced. As a result, adverse reactions that might be caused by the concomitant drug can be effectively prevented.

The compound of the present invention combined with a concomitant drug can produce excellent effects in such a way that:
(1) the dose of the compound of the present invention or a concomitant drug can be reduced as compared with single administration of the compound of the present invention or a concomitant drug;
(2) the period of treatment can be set longer by selecting a concomitant drug having a different mechanism of action from that of the compound of the present invention;
(3) sustained therapeutic effects can be achieved by selecting a concomitant drug having a different mechanism of action from that of the compound of the present invention; and
(4) synergistic effects can be obtained by a combined use of the compound of the present invention and a concomitant drug.

In the case of using the compound of the present invention and a concomitant drug in combination, the times of administration of the compound of the present invention and the concomitant drug are not limited, and the compound of the present invention and the concomitant drug may be administered simultaneously or in a staggered manner to a recipient. The dose of the concomitant drug can conform to doses clinically used and can be appropriately selected depending on a recipient, an administration route, a disease, a combination, etc.

Examples of the administration mode of the compound of the present invention and the concomitant drug include (1) administration of a single preparation obtained by simultaneously processing the compound of the present invention and the concomitant drug, (2) simultaneous administration of two preparations separately obtained from the compound of the present invention and the concomitant drug, through the same administration route, (3) administration of two preparations separately obtained from the compound of the present invention and the concomitant drug, through the same administration route in a staggered manner, (4) simultaneous administration of two preparations separately obtained from the compound of the present invention and the concomitant drug, through different administration routes, and (5) administration of two preparations separately obtained from the compound of the present invention and the concomitant drug, through different administration routes in a staggered manner (e.g., administration in the order of the compound of the present invention and the concomitant drug, or in the reverse order).

EXAMPLES

The present invention will be further described in detail by the following examples, test examples, and preparation examples, which are not intended to limit the present invention and may be modified within the scope of the present invention.

Throughout the following reference examples and examples, the term "room temperature" generally refers to a temperature of about 10° C. to about 35° C.; the "ratio" shown in a solvent mixture is a volume ratio, unless otherwise specified; and the term "%" refers to % by weight, unless otherwise specified.

The term "NH" in silica gel column chromatography indicates that aminopropyl silane-bonded silica gel was used. The term "C18" in high-performance liquid chromatography (HPLC) indicates that octadecyl-bonded silica gel was used. The "ratio" of elution solvent is a volume ratio, unless otherwise specified.

In the following reference examples and examples, the following abbreviations are used.
mp: melting point
MS: mass spectrum
$[M+H]^+$, $[M+Na]^+$, $[M-H]^+$: molecular ion peak
M: molar concentration
N: normal
$CDCl_3$: deuterated chloroform
DMSO-$d_6$: deuterated dimethyl sulfoxide
$^1H$ NMR: proton nuclear magnetic resonance
LC/MS: liquid chromatograph mass spectrometer
ESI: electrospray ionization
APCI: atmospheric pressure chemical ionization
THF: tetrahydrofuran
DMF: N,N-dimethylformamide
DMA: N,N-dimethylacetamide
DMSO: dimethyl sulfoxide
NMP: 1-methyl-2-pyrrolidone
HOBt: 1-hydroxybenzotriazole
WSC: 1-ethyl-3-(3-dimethylaminopropyl)carbodiimide
TFA: trifluoroacetic acid $^1H$ NMR was measured by Fourier transform NMR. Analysis was performed with, for example, ACD/SpecManager (trade name). Very gentle peaks of protons of, for example, hydroxyl groups and amino groups, will not be described.

MS was measured by LC/MS. As an ionization method, an ESI method or an APCI method was used. Measured values (Found) are shown as the data. In general, a molecular ion peak is observed. However, in a compound including a tert-butoxycarbonyl group, the peak observed may be of a fragment ion where a tert-butoxycarbonyl group or a tert-butyl group is removed. In addition, in a compound including a hydroxyl group, the peak observed may be of a fragment ion where $H_2O$ is removed. In a salt, generally, the peak observed is of a free molecular ion or a fragment ion.

As elemental analysis value (Anal.), the calculated value (Calcd) and the measured value (Found) are shown.

Reference Example 1

(5R)-3-(3-((4-Carbamimidamidobenzoyl)oxy)phenyl)-5-(carboxymethyl)-4,5-dihydro-1,2-oxazole-5-carboxylic acid A mixture of crude crystals of (5R)-3-(3-((4-carbamimidamidobenzoyl)oxy)phenyl)-5-(carboxymethyl)-4,5-dihydro-1,2-oxazole-5-carboxylic acid (449.4 g) and acetic acid/water (19/1) (9000 mL) was heated to 85° C. to dissolve the crystals. The insoluble precipitate was removed by filtration, and the filtrate was then heated to 80° C. A seed crystal was added thereto, and the obtained mixture was cooled to 55° C. A seed crystal was further added thereto, then acetone (1350 mL) was added dropwise thereto, and the obtained mixture was stirred at 50° C. for 30 minutes. Acetone (450 mL) was further added dropwise thereto, and the obtained mixture was stirred at 50° C. for 15 minutes. Acetone (7200 mL) was further added dropwise thereto, and the obtained mixture was stirred at 50° C. for 2 hours, then gradually cooled to room temperature, and stirred overnight. The solid was collected by filtration, washed with acetone (9000 mL), and then dried under reduced pressure at 85° C. for 4 hours to obtain the title compound (297 g).

$^1$H NMR (400 MHz, DMSO-$d_6$) δ 2.72-2.85 (2H, m), 3.19 (1H, d, J=16.6 Hz), 3.90 (1H, d, J=17.1 Hz), 7.34-7.45 (3H, m), 7.52-7.63 (3H, m), 7.72 (4H, brs), 8.17 (2H, d, J=8.7 Hz).

MS: [M+H]$^+$ 427.1.

Powder X-ray diffractometry was conducted under the following conditions.
Measurement apparatus: RIGAKU Ultima IV
Measurement conditions:
  Cu-Kα radiation: λ=1.5418 angstroms
  Tube volume: 40 kV
  Tube current: 50 mA
  Scan speed: 6°/min
  Scan angle (2θ): 2 to 35°
Interplanar spacing (d) data: 14.92±0.5, 7.12±0.1, 6.31±0.1, 5.41±0.1, 5.13±0.1, 4.78±0.1, 4.38±0.1, 4.21±0.1, 4.02±0.1, 3.87±0.1, 3.66±0.1, and 3.55±0.1 angstroms.

Reference Example 2

(5R)-3-(3-((4-Carbamimidamidobenzoyl)oxy)phenyl)-5-(carboxymethyl)-4,5-dihydro-1,2-oxazole-5-carboxylic acid dihydrate A mixture of (5R)-3-(3-((4-carbamimidamidobenzoyl)oxy)phenyl)-5-(carboxymethyl)-4,5-dihydro-1,2-oxazole-5-carboxylic acid (317 g) and acetic acid/water (1/1) (9510 mL) was heated to 80° C. to dissolve the crystals. Water (3170 mL) was added dropwise thereto at an internal temperature of 73° C. or higher, a seed crystal was added thereto, and water (3170 mL) was then added dropwise thereto at an internal temperature of 73° C. or higher. The obtained mixture was cooled to 60° C. over 1 hour, stirred at 60° C. for 1 hour, then cooled to 40° C. over 2 hours, and stirred at 40° C. for 2 hours. Then, the mixture was gradually cooled to room temperature and was stirred at room temperature overnight. The solid was collected by filtration and was washed with water (6000 mL) and subsequently with acetone (4000 mL) to obtain crystals (314 g). The obtained crystals were filtered and were then pulverized with a jet mill to obtain the title compound (307.4 g).

$^1$H NMR (400 MHz, DMSO-$d_6$) δ 2.65-2.94 (2H, m), 3.19-3.42 (1H, m), 3.91 (1H, d, J=17.1 Hz), 7.34-7.43 (3H, m), 7.51-7.64 (3H, m), 7.98 (4H, brs), 8.16 (2H, d, J=8.4 Hz).

MS: [M+H]$^+$ 427.2.

Powder X-ray diffractometry was conducted under the following conditions.
Measurement apparatus: RIGAKU Ultima IV
Measurement conditions:
  Cu-Kα radiation: λ=1.5418 angstroms
  Tube volume: 40 kV
  Tube current: 50 mA
  Scan speed: 6°/min
  Scan angle (2θ) : 2 to 35°
Interplanar spacing (d) data: 12.99±0.5, 8.43±0.1, 6.50±0.1, 5.49±0.1, 5.37±0.1, 4.86±0.1, 4.33±0.1, 4.12±0.1, 3.99±0.1, 3.87±0.1, 3.73±0.1, 3.56±0.1, and 3.37±0.1 angstroms.

Example 1

2-(((6-((4-Carbamimidamidobenzoyl)oxy)-2,3-dihydro-1-benzofuran-4-yl)carbonyl)amino)ethanesulfonic acid A) Ethyl 3-(benzyloxy)-5-hydroxybenzoate Potassium carbonate (76 g) and benzyl bromide (33 mL) were added to a mixture of ethyl 3,5-hydroxybenzoate (50 g) and DMF (250 mL) at 0° C., followed by stirring at room temperature overnight. The reaction mixture was poured into a mixture of ethyl acetate and 1 M hydrochloric acid at 0° C., followed by extraction with ethyl acetate. The organic layer was washed with water, a saturated sodium hydrogen carbonate aqueous solution, and a saturated saline solution and was then dried over anhydrous sodium sulfate, and the solvent was distilled under reduced pressure. The residue was purified by silica gel column chromatography (ethyl acetate/hexane) to obtain the title compound (23.19 g).

MS: [M-H]$^+$ 271.1.

B) Ethyl 3-(benzyloxy)-5-(2,2-diethoxyethoxy)benzoate

A mixture of ethyl 3-(benzyloxy)-5-hydroxybenzoate (105 g), 2-bromo-1,1-diethoxyethane (114 g), potassium carbonate (64.0 g), potassium iodide (6.40 g), and DMA (500 mL) was stirred at 160° C. for 15 hours. Water was added to the reaction mixture, followed by extraction with ethyl acetate. The organic layer was washed with water and a saturated saline solution and was then dried over anhydrous magnesium sulfate, and the solvent was distilled under reduced pressure. The residue was purified by silica gel column chromatography (ethyl acetate/hexane) to obtain the title compound (132 g).

MS: [M-H]$^+$ 387.3.

C) Ethyl 6-(benzyloxy)benzofuran-4-carboxylate

A mixture of ethyl 3-(benzyloxy)-5-(2,2-diethoxyethoxy)benzoate (132 g), polyphosphoric acid (66 g), and toluene (600 mL) was stirred at 100° C. for 1.5 hours. The reaction mixture was poured into ice, followed by extraction with ethyl acetate. The organic layer was washed with water and a saturated saline solution and was then dried over anhydrous magnesium sulfate, and the solvent was distilled under reduced pressure. The residue was purified by silica gel column chromatography (ethyl acetate/hexane) to obtain the title compound (63.1 g).
MS: [M+H]$^+$ 297.1.

D) Ethyl 6-hydroxy-2,3-dihydrobenzofuran-4-carboxylate

A mixture of ethyl 6-(benzyloxy)benzofuran-4-carboxylate (70 g), 10% palladium on carbon (7 g, water content: about 50%), ethanol (700 mL), acetic acid (280 mL), and THF (280 mL) was stirred under a hydrogen atmosphere at room temperature overnight. The catalyst was removed by filtration, and the filtrate was then concentrated under reduced pressure. Diisopropyl ether (120 mL) and heptane (120 mL) were added to the residue, followed by stirring at room temperature for 2 hours. The precipitated solid was collected by filtration and was washed with diisopropyl ether/heptane (50 mL/50 mL) to obtain the title compound (44.6 g).
MS: [M+H]$^+$ 209.0.

E) 6-Hydroxy-2,3-dihydrobenzofuran-4-carboxylic acid

A 2 N sodium hydroxide aqueous solution (612 mL) was added to a mixture of ethyl 6-hydroxy-2,3-dihydrobenzofuran-4-carboxylate (85 g), THF (425 mL), and ethanol (425 mL) at room temperature, followed by stirring at 60° C. for 2 hours. The solvent was distilled under reduced pressure, and the residue was then neutralized by the addition of 2 N hydrochloric acid at 0° C., followed by extraction with ethyl acetate/THF (400 mL/200 mL). The extract was washed with water (600 mL) and a saturated saline solution (600 mL) and was then dried over anhydrous magnesium sulfate, and the solvent was distilled under reduced pressure to obtain the title compound (75 g).
MS: [M+H]$^+$ 181.0.

F) Benzyl 6-hydroxy-2,3-dihydrobenzofuran-4-carboxylate

Benzyl bromide (112 mL) was added to a mixture of 6-hydroxy-2,3-dihydrobenzofuran-4-carboxylic acid (162 g), N,N-diisopropylethylamine (236 mL), and DMF (1600 mL) at room temperature, followed by stirring at the same temperature for 1 day. A 5% citric acid aqueous solution (1000 mL) and water (600 mL) were added to the reaction mixture, followed by extraction with ethyl acetate (three times with 1500 mL, 1000 mL, and 500 mL, respectively). The extract was washed with water (1000 mL) and a saturated saline solution (1000 mL) and was passed through a NH silica gel pad (ethyl acetate/hexane), and the solvent was then distilled under reduced pressure. Diisopropyl ether (80 mL) and heptane (1300 mL) were added to the residue, followed by stirring at room temperature for 1 hour. The precipitated solid was collected by filtration to obtain the title compound (224 g).
MS: [M+H]$^+$ 271.0.

G) Benzyl 6-((4-nitrobenzoyl)oxy)-2,3-dihydrobenzofuran-4-carboxylate p-Nitrobenzoyl chloride (117 g) was added to a mixture of benzyl 6-hydroxy-2,3-dihydrobenzofuran-4-carboxylate (113.2 g) and pyridine (1000 mL) at room temperature, followed by stirring at 60° C. for 1 hour. Water (3000 mL) was added to the reaction mixture at 0° C., followed by stirring at room temperature for 30 minutes. The precipitated solid was collected by filtration and was washed with water to obtain the title compound (174 g).
$^1$H NMR (400 MHz, DMSO-d$_6$) δ 3.48 (2H, t, J=8.7 Hz), 4.65 (2H, t, J=8.8 Hz), 5.35 (2H, s), 7.12 (1H, d, J=2.1 Hz), 7.33-7.44 (4H, m), 7.45-7.50 (2H, m), 8.32-8.43 (4H, m).

H) 6-((4-Aminobenzoyl)oxy)-2,3-dihydrobenzofuran-4-carboxylic acid

A mixture of benzyl 6-((4-nitrobenzoyl)oxy)-2,3-dihydrobenzofuran-4-carboxylate (43.5 g), 10% palladium on carbon (4.3 g, water content: about 50%), and THF (1000 mL) was stirred under a hydrogen atmosphere at room temperature for 18 hours. The catalyst was removed by filtration, and the filtrate was then concentrated under reduced pressure to obtain the title compound (29.5 g).
MS: [M+H]$^+$ 300.1.

I) 6-((4-Guanidinobenzoyl)oxy)-2,3-dihydrobenzofuran-4-carboxylic acid

A mixture of cyanamide (24.86 g) and tert-butyl alcohol (360 mL) was added to a mixture of 6-((4-aminobenzoyl)oxy)-2, 3-dihydrobenzofuran-4-carboxylic acid (59 g), 4 N hydrogen chloride/cyclopentyl methyl ether (148 mL), and THF (1200 mL) at room temperature, followed by stirring at 60° C. overnight. A mixture of water (1200 mL), THF (600 mL), ammonium acetate (45.6 g), and water (1200 mL) was added to the reaction mixture at room temperature, followed by stirring at the same temperature for 1 hour. The precipitated solid was collected by filtration and was washed with methyl ethyl ketone (600 mL) and THF (600 mL) to obtain the title compound (69.7 g).
MS: [M+H]$^+$ 342.0.

J) 2-(((6-((4-Carbamimidamidobenzoyl)oxy)-2,3-dihydro-1-benzofuran-4-yl)carbonyl)amino)ethanesulfonic acid WSC hydrochloride (50.5 g), HOBt·H$_2$O (40.4 g), and 6-((4-guanidinobenzoyl)oxy)-2,3-dihydrobenzofuran-4-carboxylic acid (60 g) were added to a mixture of 2-aminoethanesulfonic acid (33.0 g), N,N-diisopropylethylamine (120 mL), DMF (300 mL), and DMSO (300 mL) at room temperature, followed by stirring at the same temperature overnight. 6-((4-Guanidinobenzoyl)oxy)-2,3-dihydrobenzofuran-4-carboxylic acid (60 g) was reacted in the same way. 1 N hydrochloric acid was added to each reaction mixture at 18° C. or lower, followed by stirring at the same temperature for 1 hour. The precipitated solids were combined, collected by filtration, washed with water (600 mL×2) and acetonitrile (600 mL), and then dried under reduced pressure to obtain the title compound (113 g) as a crude product.

The crude product (307 g) synthesized by the same method as above was dissolved in DMSO/acetic acid (2700 mL/300 mL), and methyl ethyl ketone (2100 mL) was added dropwise thereto at 50° C., followed by stirring at the same temperature for 1 hour and subsequently at room temperature for 30 minutes. The precipitated solid was collected by filtration and was washed with methyl ethyl ketone/DMSO (2:1, 1000 mL) and methyl ethyl ketone (1500 mL) to obtain the title compound (283 g) as a solid.

A mixture of the solid (275 g) thus obtained and DMSO/acetic acid (2500 mL/275 mL) was stirred at 60° C. for 2 hours and subsequently at room temperature overnight, and methyl ethyl ketone (2000 mL) was then added dropwise thereto at room temperature. The precipitated solid was collected by filtration, washed with water (3000 mL) and acetone (500 mL), and then dried under reduced pressure at 50° C. to obtain crystals of the title compound (226.5 g).
$^1$H NMR (300 MHz, DMSO-$d_6$) δ 2.66 (2H, t, J=6.6 Hz), 3.37-3.55 (4H, m), 4.61 (2H, t, J=8.7 Hz), 6.88 (1H, d, J=1.9 Hz), 6.95 (1H, d, J=2.3 Hz), 7.39-7.46 (2H, m), 7.70 (4H, brs), 8.13-8.18 (2H, m), 8.34 (1H, t, J=5.1 Hz), 10.00 (1H, brs).

Example 4

(((((6-((4-Carbamimidobenzoyl)oxy)-2,3-dihydro-1-benzofuran-4-yl)carbonyl)amino)methyl) phosphonic acid hydrochloride A) Diethyl ((6-hydroxy-2,3-dihydrobenzofuran-4-carboxamido)methyl)phosphonate Diethyl (aminomethyl)phosphonate (209 mg), N,N-diisopropylethylamine (0.436 mL), WSC hydrochloride (239 mg), and HOBt·$H_2O$ (191 mg) were added to a mixture of 6-hydroxy-2,3-dihydrobenzofuran-4-carboxylic acid (150 mg) and DMF (3 mL) at room temperature, followed by stirring at the same temperature overnight. Water was added to the reaction mixture, followed by extraction with ethyl acetate/THF. The extract was washed with 1 N hydrochloric acid (2 mL) and a saturated saline solution and was then dried over anhydrous magnesium sulfate, and the solvent was distilled under reduced pressure. The residue was purified by silica gel column chromatography (ethyl acetate/hexane and subsequently methanol/ethyl acetate) to obtain the title compound (254 mg).
MS: [M+H]$^+$ 330.1.

B) 4-H(Diethoxyphosphoryl)methyl)carbamoyl)-2,3-dihydrobenzofuran-6-yl 4-guanidinobenzoate trifluoroacetate 4-Guanidinobenzoyl chloride hydrochloride (361 mg) was added in two divided portions to a mixture of diethyl ((6-hydroxy-2,3-dihydrobenzofuran-4-carboxamido) methyl)phosphonate (254 mg), NMP (0.4 mL), and pyridine (0.4 mL) at 50° C., followed by stirring at the same temperature for 2 hours. The reaction mixture was purified by HPLC (C18, mobile phase: water/acetonitrile (system containing 0.1% TFA)) to obtain the title compound (378 mg).
MS: [M+H]$^+$ 491.2.

C) (((((6-((4-Carbamimidobenzoyl)oxy)-2,3-dihydro-1-benzofuran-4-yl)carbonyl)amino)methyl) phosphonic acid hydrochloride A mixture of 4-(((diethoxyphosphoryl)methyl)carbamoyl)-2,3-dihydrobenzofuran-6-yl 4-guanidinobenzoate trifluoroacetate (378 mg), 6 N hydrochloric acid (1 mL), and THF (1 mL) was stirred at 60° C. for 4 hours. The reaction mixture was concentrated under reduced pressure, and the solid was washed with water and acetonitrile to obtain the title compound (215 mg).
$^1$H NMR (400 MHz, DMSO-$d_6$) δ 3.41 (2H, t, J=8.9 Hz), 3.51 (2H, dd, J=12.1, 6.1 Hz), 4.61 (2H, t, J=8.7 Hz), 6.88 (1H, s), 7.09 (1H, s), 7.43 (2H, d, J=8.4 Hz), 7.76 (4H, s), 8.15 (2H, d, J=8.5 Hz), 8.36 (1H, brs), 10.23 (1H, brs).

Example 6

3-(6-((4-Carbamimidobenzoyl)oxy)-2,3-dihydro-1-benzofuran-4-yl)-5-(carboxymethyl)-4,5-dihydro-1,2-oxazole-5-carboxylic acid A) Ethyl 6-(benzyloxy)-2,3-dihydro-1-benzofuran-4-carboxylate A mixture of ethyl 6-hydroxy-2,3-dihydro-1-benzofuran-4-carboxylate (1.50 g), benzyl bromide (1.027 mL), potassium carbonate (1.195 g), and DMF (15 mL) was stirred at 70° C. for 4 days. Water was added to the reaction mixture, followed by extraction with ethyl acetate. The extract was washed with a saturated saline solution and was dried over anhydrous magnesium sulfate, and the solvent was then distilled under reduced pressure. The residue was purified by silica gel column chromatography (ethyl acetate/hexane) to obtain the title compound (1.58 g).
$^1$H NMR (400 MHz, DMSO-$d_6$) δ 1.31 (3H, t, J=7.1 Hz), 3.36 (2H, t, J=8.7 Hz), 4.28 (2H, q, J=7.2 Hz), 4.56 (2H, t, J=8.7 Hz), 5.11 (2H, s), 6.74 (1H, d, J=2.0 Hz), 6.99 (1H, d, J=2.1 Hz), 7.27-7.53 (5H, m).

B) (6-(Benzyloxy)-2,3-dihydro-1-benzofuran-4-yl) methanol

A mixture of ethyl 6-(benzyloxy)-2,3-dihydro-1-benzofuran-4-carboxylate (1.58 g) and THF (15 mL) was added dropwise to a mixture of lithium aluminum hydride (0.241 g) and THF (15 mL) at 0° C., followed by stirring at the same temperature for 2 hours. Sodium sulfate decahydrate was added thereto at 0° C. The precipitate was removed by filtration, and the filtrate was then concentrated under reduced pressure to obtain the title compound (1.35 g).
$^1$H NMR (400 MHz, DMSO-$d_6$) δ 3.02 (2H, t, J=7.9 Hz), 4.38 (2H, d, J=4.6 Hz), 4.50 (2H, t, J=7.7 Hz), 4.94-5.20 (3H, m), 6.33 (1H, brs), 6.50 (1H, brs), 7.22-7.59 (5H, m).

C) 6-(Benzyloxy)-2,3-dihydro-1-benzofuran-4-carbaldehyde

A mixture of a sulfur trioxide-pyridine complex (2.52 g) and DMSO (20 mL) was added dropwise to a mixture of (6-(benzyloxy)-2,3-dihydro-1-benzofuran-4-yl)methanol (1.35 g), triethylamine (3.67 mL), and DMSO (10 mL) at room temperature, followed by stirring at the same temperature overnight. Water was added to the reaction mixture, followed by extraction with ethyl acetate. The extract was washed with 1 M hydrochloric acid and a saturated saline solution and was dried over anhydrous magnesium sulfate, and the solvent was then distilled under reduced pressure to obtain the title compound (1.31 g).
$^1$H NMR (400 MHz, DMSO-$d_6$) δ 3.39 (2H, t, J=8.7 Hz), 4.62 (2H, t, J=8.7 Hz), 5.14 (2H, s), 6.80 (1H, s), 7.03 (1H, s), 7.23-7.54 (5H, m), 9.98 (1H, s).

D) (E)-1-(6-(Benzyloxy)-2,3-dihydro-1-benzofuran-4-yl)-N-hydroxymethanimine

A mixture of 6-(benzyloxy)-2,3-dihydro-1-benzofuran-4-carbaldehyde (1.31 g), hydroxylammonium chloride (0.394 g), sodium hydrogen carbonate (0.476 g), and ethanol (15 mL) was stirred at room temperature overnight. Water and a saturated saline solution were added to the reaction mixture, followed by extraction with ethyl acetate. The extract was washed with a saturated saline solution and was dried over anhydrous magnesium sulfate, and the solvent was then distilled under reduced pressure. The residue was purified by silica gel column chromatography (ethyl acetate/hexane) to obtain the title compound (1.11 g).
MS: [M+H]$^+$ 270.2.

E) tert-Butyl 3-(6-(benzyloxy)-2,3-dihydro-1-benzo-furan-4-yl)-5-(2-tert-butoxy-2-oxoethyl)-4,5-dihydro-1,2-oxazole-5-carboxylate A sodium hypochlorite aqueous solution (5%, 1.824 g) was added dropwise to a mixture of (E)-1-(6-(benzyloxy)-2,3-dihydro-1-benzofuran-4-yl)-N-hydroxymethanimine (300 mg), di-tert-butyl 2-methylene succinate (270 mg), and THF (3 mL) at 0° C., followed by stirring at 0° C. for 2 hours and subsequently at room temperature for 3 days. The reaction mixture was diluted with ethyl acetate, and water was then added thereto. The organic layer was washed with a saturated saline solution and was dried over anhydrous magnesium sulfate, and the solvent was then distilled under reduced pressure. The residue was purified by silica gel column chromatography (ethyl acetate/hexane) to obtain the title compound (367 mg).
MS: [M+Na]$^+$ 532.3.

F) tert-Butyl 5-(2-tert-butoxy-2-oxoethyl)-3-(6-hydroxy-2,3-dihydro-1-benzofuran-4-yl)-4,5-dihydro-1,2-oxazole-5-carboxylate A mixture of tert-butyl 3-(6-(benzyloxy)-2,3-dihydro-1-benzofuran-4-yl)-5-(2-tert-butoxy-2-oxoethyl)-4,5-dihydro-1,2-oxazole-5-carboxylate (367 mg), 10% palladium on carbon (36 mg, water content: about 55%), and THF (4 mL) was stirred under a hydrogen atmosphere at room temperature overnight. The catalyst was removed by filtration, and the filtrate was then concentrated under reduced pressure. The residue was purified by silica gel column chromatography (ethyl acetate/hexane) to obtain the title compound (265 mg).
MS: [M+Na]$^+$ 442.1.

G) tert-Butyl 5-(2-tert-butoxy-2-oxoethyl)-3-(6-((4-carbamimidamidobenzoyl)oxy)-2,3-dihydro-1-benzofuran-4-yl-4,5-dihydro-1,2-oxazole-5-carboxylate 4-Carbamimidamidobenzoyl chloride hydrochloride (148 mg) was added to a mixture of tert-butyl 5-(2-tert-butoxy-2-oxoethyl)-3-(6-hydroxy-2,3-dihydro-1-benzofuran-4-yl)-4,5-dihydro-1,2-oxazole-5-carboxylate (265 mg), pyridine (0.3 mL), and NMP (0.3 mL) at 50° C., followed by stirring at the same temperature for 30 minutes. 4-Carbamimidamidobenzoyl chloride hydrochloride (148 mg) was further added thereto, followed by stirring at 50° C. overnight. The reaction mixture was purified by HPLC (C18, mobile phase: water/acetonitrile (system containing 0.1% TFA)), and a saturated sodium hydrogen carbonate aqueous solution was added to the obtained fraction, followed by extraction with ethyl acetate. The extract was dried over anhydrous magnesium sulfate, and the solvent was distilled under reduced pressure to obtain the title compound (155 mg).
MS: [M+H]$^+$ 581.3.

H) 3-(6-((4-Carbamimidamidobenzoyl)oxy)-2,3-dihydro-1-benzofuran-4-yl)-5-(carboxymethyl)-4,5-dihydro-1,2-oxazole-5-carboxylic acid trifluoroacetate A mixture of tert-butyl 5-(2-tert-butoxy-2-oxoethyl)-3-(6-((4-carbamimidamidobenzoyl)oxy)-2,3-dihydro-1-benzofuran-4-yl)-4,5-dihydro-1,2-oxazole-5-carboxylate (155 mg) and TFA (2 mL) was stirred at room temperature overnight. The reaction mixture was concentrated under reduced pressure, and the residue was then washed with diethyl ether to obtain the title compound (118 mg).
$^1$H NMR (400 MHz, DMSO-d$_6$) δ 2.97 (2H, brs), 3.25-3.42 (2H, m), 3.52 (1H, d, J=18.2 Hz), 3.89 (1H, d, J=17.4 Hz), 4.64 (2H, t, J=8.7 Hz), 6.87 (1H, s), 6.97 (1H, s), 7.43 (2H, d, J=8.4 Hz), 7.78 (4H, brs), 8.15 (2H, d, J=8.5 Hz), 10.17 (1H, brs), 13.05 (1H, s), 13.29 (1H, s).

I) 3-(6-((4-Carbamimidamidobenzoyl)oxy)-2,3-dihydro-1-benzofuran-4-yl)-5-(carboxymethyl)-4,5-dihydro-1,2-oxazole-5-carboxylic acid 6 M hydrochloric acid (0.1 mL) was added to a mixture of 3-(6-((4-carbamimidamidobenzoyl)oxy)-2,3-dihydro-1-benzofuran-4-yl)-5-(carboxymethyl)-4,5-dihydro-1,2-oxazole-5-carboxylic acid trifluoroacetate (98.0 mg) and water (5 mL) at room temperature. Subsequently, an ammonium acetate aqueous solution was added to the mixture to adjust the pH to about 4, followed by stirring at room temperature overnight. The precipitated solid was collected by filtration and was washed with water and acetone to obtain the title compound (72.3 mg).
$^1$H NMR (400 MHz, DMSO-d$_6$) δ 2.76 (2H, s), 3.19 (1H, d, J=17.1 Hz), 3.25-3.39 (2H, m), 3.89 (1H, d, J=17.0 Hz), 4.63 (2H, t, J=8.7 Hz), 6.83 (1H, d, J=1.2 Hz), 6.91 (1H, d, J=1.6 Hz), 7.37 (2H, d, J=8.6 Hz), 7.74 (4H, brs), 8.12 (2H, d, J=8.6 Hz).

In Examples 2, 3 and 5, compounds were produced by the methods described above or in accordance with the methods. The example compounds are shown in the following table. The column "MS" in the table shows measured values.

TABLE 1

| EXAMPLE | IUPAC NAME | STRUCTURE | SALT | MS |
|---|---|---|---|---|
| 1 | 2-(((6-((4-carbamimidamindobenzoyl)oxy)-2,3-dihydro-1-benzofuran-4-yl)carbonyl)amino)ethanesulfonic acid | 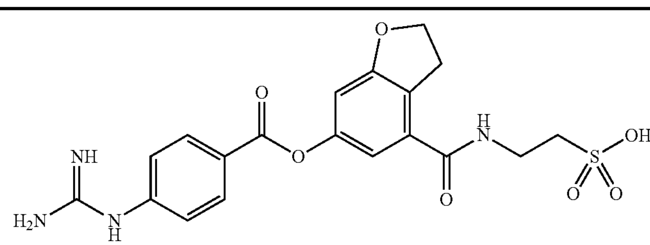 | | 448.9 |

TABLE 1-continued

| EXAMPLE | IUPAC NAME | STRUCTURE | SALT | MS |
|---|---|---|---|---|
| 2 | 3-(((6-((4-carbamimidamindobenzoyl)oxy)-2,3-dihydro-1-benzofuran-4-yl)carbonyl)amino)propane-1-sulfonic acid | 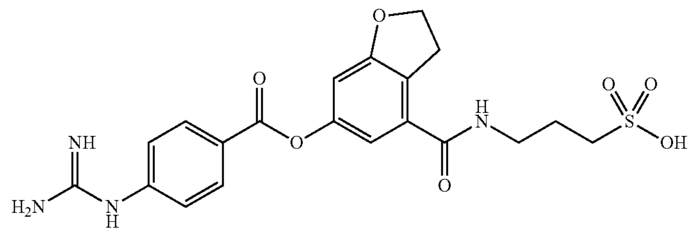 [SMILES: N=C(N)Nc1ccc(C(=O)Oc2cc3c(c(C(=O)NCCCS(=O)(=O)O)c2)CCO3)cc1] | | 462.9 |
| 3 | (((6-((4-carbamimidamindobenzoyl)oxy)-2,3-dihydro-1-benzofuran-4-yl)carbonyl)amino)methanesulfonic acid | 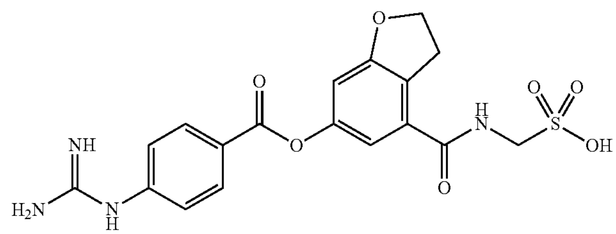 [SMILES: N=C(N)Nc1ccc(C(=O)Oc2cc3c(c(C(=O)NCS(=O)(=O)O)c2)CCO3)cc1] | | 434.9 |
| 4 | ((((6-((4-carbamimidamindobenzoyl)oxy)-2,3-dihydro-1-benzofuran-4-yl)carbonyl)amino)methyl)phosphonic acid | 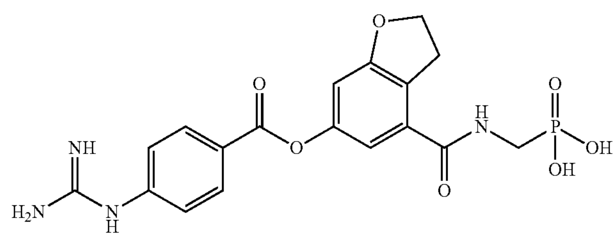 [SMILES: N=C(N)Nc1ccc(C(=O)Oc2cc3c(c(C(=O)NCP(=O)(O)O)c2)CCO3)cc1] | HCl | 435.1 |
| 5 | 3-(6-((4-carbamimidamindobenzoyl)oxy)-2,2-dimethyl-2,3-dihydro-1-benzofuran-4-yl)-5-(carboxymethyl)-4,5-dihydro-1,2-oxazole-5-carboxylic acid | 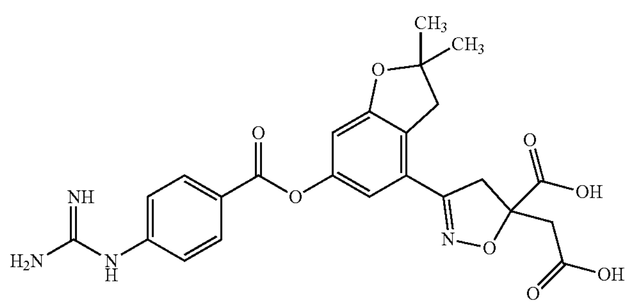 [SMILES: CC1(C)Cc2c(cc(OC(=O)c3ccc(NC(=N)N)cc3)cc2C2=NOC(CC(=O)O)(C(=O)O)C2)O1] | | 497.1 |
| 6 | 3-(6-((4-carbamimidamindobenzoyl)oxy)-2,3-dihydro-1-benzofuran-4-yl)-5-(carboxymethyl)-4,5-dihydro-1,2-oxazole-5-carboxylic acid | 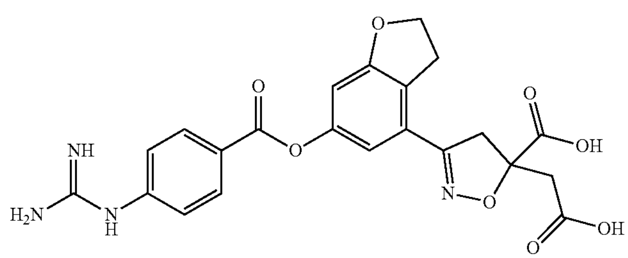 [SMILES: N=C(N)Nc1ccc(C(=O)Oc2cc3c(c(C4=NOC(CC(=O)O)(C(=O)O)C4)c2)CCO3)cc1] | | 469.1 |

Test Example 1

Human Enteropeptidase Inhibitory Activity

Human recombinant enteropeptidase (#REN-260, ITSI-Biosciences LLC) was diluted with an assay buffer (50 mM Tricine, pH 8.0, 0.01 (w/v) %, Tween 20, 10 mM $CaCl_2$) to prepare a 24 mU/mL enzyme solution. Subsequently, 5FAM-Abu-Gly-Asp-Asp-Asp-Lys-Ile-Val-Gly-Gly-Lys (CPQ2)-Lys-Lys-$NH_2$ (purity: 97.2%, CPC Scientific Inc., SEQ ID NO: 1) was diluted with the assay buffer to prepare a 2.1 μM substrate solution. A test compound is dissolved in DMSO into a 1 mM solution, and the solution was diluted by 100-fold with the assay buffer to give a compound solution. To a 384-well black plate (#784076, Greiner Bio-One), 5 μL of the compound solution and 5 μL of the substrate solution were added and mixed, and 5 μL of the enzyme solution was then added to the mixture, followed by mixing to start the reaction. The fluorescence intensity was measured with a fluorescence plate reader EnVision (The Perkin-Elmer Corp.) at an excitation wavelength of 485 nm and a fluorescence wavelength of 535 nm. The same reaction as above except that the test compound was not contained was performed (test compound non-addition group). Furthermore, the same reaction as above except that the test compound and the enzyme were not contained was performed (control group). The inhibition rate was calculated using the fluorescence intensity at 2 hours after the start of the reaction by the following expression:

Inhibition rate (%)=(1-((fluorescence intensity of test compound addition group)−(fluorescence intensity of control group))/((fluorescence intensity of test compound non-addition group)−(fluorescence intensity of control group)))×100

The results are shown in Table 2.

TABLE 2

| Test compound (Example No.) | Inhibition rate at 3.3 µM |
| --- | --- |
| 1 | 101% |
| 2 | 101% |
| 3 | 101% |
| 4 | 101% |
| 5 | 100% |
| 6 | 101% |

As shown above, it was demonstrated that the invention compounds have excellent enteropeptidase inhibitory activities.

Test Example 2

Fecal Protein Concentration-Increasing Test Using HFD-Fed Mouse

High fat diet-fed (HFD-fed) mice (D12079B diet, male, 19-week old) were orally administered with a 0.5% methyl cellulose suspension containing a test compound (10 mg/kg) (compound administration group, six mice per group) or a 0.5% methyl cellulose suspension (compound non-administration group (vehicle), five mice per group), and whole feces were collected on the first day of administration. Dried feces were dissolved in 0.5 N NaOH, followed by centrifugation at 12,000 rpm. The protein concentration in the supernatant was then quantitatively measured (Lowry method), and the amount of protein contained in 1 g of feces was calculated as the fecal protein concentration (mg/g feces). The average of each group is shown below.

TABLE 3

| Test compound | Dose of compound (mg/kg) | Fecal protein concentration (mg/g feces) |
| --- | --- | --- |
| vehicle | 0 | 115.0 |
| Example 1 | 10 | 188.8 |

As shown above, it was demonstrated that the invention compounds have an effect of increasing the fecal protein concentration by enteropeptidase inhibitory activities.

Test Example 3

Anti-Obesity Effect Test Using DIO Mouse

Diet-induced obesity (DIO) mice (D12079B diet, male, 32-week old) were orally administered with a 0.5% methyl cellulose suspension containing a test compound (30 mg/kg) (compound administration group, six mice per group) or a 0.5% methyl cellulose suspension (compound non-administration group (vehicle), six mice per group) once a day for eight days. The averages of the body weights at the start of administration and after continuous administration for eight days are shown below.

TABLE 4

| | | Body weight (g) | |
| --- | --- | --- | --- |
| Test compound | Dose of compound (mg/kg) | At start of administration | After continuous administration for 8 days |
| vehicle | 0 | 42.9 | 43.4 |
| Example 1 | 30 | 43.5 | 42.8 |

As shown above, it was demonstrated that the invention compounds show an effect of decreasing body weight and have an anti-obesity effect by enteropeptidase inhibitory activities.

Formulation Example 1

Production of Capsule

| 1) Compound of Example 1 | 30 mg |
| --- | --- |
| 2) Fine cellulose powder | 10 mg |
| 3) Lactose | 19 mg |
| 4) Magnesium stearate | 1 mg |
| Total: | 60 mg |

Ingredients 1), 2), 3), and 4) are mixed and filled in a gelatin capsule shell.

Formulation Example 2

Production of Tablet

| 1) Compound of Example 1 | 30 g |
| --- | --- |
| 2) Lactose | 50 g |
| 3) Corn starch | 15 g |
| 4) Carboxymethylcellulose calcium | 44 g |
| 5) Magnesium stearate | 1 g |
| Total of 1000 tablets: | 140 g |

The whole amounts of ingredients 1), 2), and 3) and 30 g of ingredient 4) are kneaded with water and granulated after vacuum drying. The granulated powders are mixed with 14 g of ingredient 4) and 1 g of ingredient 5). The mixture is compressed using a tableting machine. In this way, 1000 tablets each containing 30 mg of the compound of Example 1 are obtained.

INDUSTRIAL APPLICABILITY

The invention compounds have excellent enteropeptidase inhibitory activities and are useful in the treatment or prevention of, for example, obesity or diabetes mellitus.

All publications, patent publications, and patent application publications cited in this specification are herein incorporated by reference in their entirety.

SEQUENCE LISTING FREE TEXT

SEQ ID NO: 1: synthetic peptide

The invention claimed is:

1. A compound represented by the formula (I) or a salt thereof:

[Formula 1]

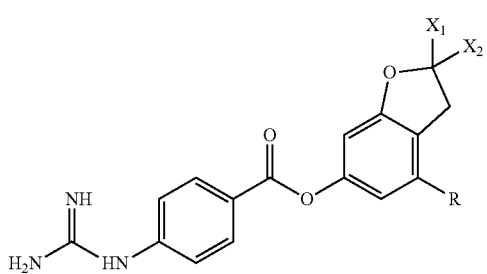

(I)

wherein
R represents

[Formula 2]

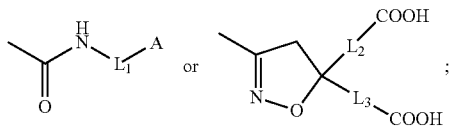

$L_1$ represents a $C_{1-6}$ alkylene group;
$L_2$ and $L_3$ are the same or different and each represent a bond or a $C_{1-6}$ alkylene group;
A represents $-S(O)_2OH$ or $-P(O)(OH)_2$; and
$X_1$ and $X_2$ are the same or different and each represent H or a $C_{1-6}$ alkyl group.

2. The compound according to claim 1 or a salt thereof, wherein R is

[Formula 3]

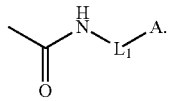

3. The compound according to claim 1 or a salt thereof, wherein $L_1$ is a $C_{1-3}$ alkylene group.

4. The compound according to claim 1 or a salt thereof, wherein A is $-S(O)_2OH$.

5. The compound according to claim 1 or a salt thereof, wherein R is

[Formula 4]

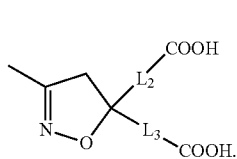

6. The compound according to claim 1 or a salt thereof, wherein $L_2$ is a bond, and $L_3$ is a $C_{1-3}$ alkylene group.

7. The compound according to claim 1 or a salt thereof, wherein $X_1$ and $X_2$ are the same or different and each represent H or a $C_{1-3}$ alkyl group.

8. The compound according to claim 1 or a salt thereof, wherein
R is

[Formula 5]

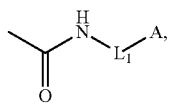

$L_1$ is a $C_{1-3}$ alkylene group, and both of $X_1$ and $X_2$ are H.

9. The compound according to claim 1 or a salt thereof, wherein

R is

[Formula 6]

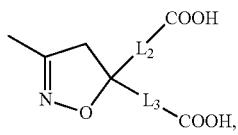

$L_2$ is a bond, $L_3$ is a $C_{1-3}$ alkylene group, and both of $X_1$ and $X_2$ are H or both of $X_1$ and $X_2$ are a $C_{1-3}$ alkyl group.

10. 2-(((6-((4-Carbamimidamidobenzoyl)oxy)-2,3-dihydro-1-benzofuran-4-yl)carbonyl)amino)ethanesulfonic acid or a salt thereof.

11. ((((6-((4-Carbamimidamidobenzoyl)oxy)-2,3-dihydro-1-benzofuran-4-yl)carbonyl)amino)methyl)phosphonic acid or a salt thereof.

12. 3-(6-((4-Carbamimidamidobenzoyl)oxy)-2,3-dihydro-1-benzofuran-4-yl)-5-(carboxymethyl)-4,5-dihydro-1,2-oxazole-5-carboxylic acid or a salt thereof.

13. A medicament comprising a compound according to claim 1 or a salt thereof.

14. The medicament according to claim 13, wherein the medicament is an agent for preventing or treating obesity.

15. The medicament according to claim 13, wherein the medicament is an agent for treating diabetes mellitus.

16. A method for treating obesity or diabetes mellitus in a mammal, comprising administering an effective amount of a compound according to claim 1 or a salt thereof to the mammal.

* * * * *

```
                     SEQUENCE LISTING

<160> NUMBER OF SEQ ID NOS: 1

<210> SEQ ID NO 1
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa stands for Abu (2-Aminobutyric acid)
<220> FEATURE:
<221> NAME/KEY: MOD_RES
<222> LOCATION: (1)..(1)
<223> OTHER INFORMATION: modified with 5FAM
<220> FEATURE:
<221> NAME/KEY: MOD_RES
<222> LOCATION: (11)..(11)
<223> OTHER INFORMATION: modified with CPQ2

<400> SEQUENCE: 1

Xaa Gly Asp Asp Asp Lys Ile Val Gly Gly Lys Lys Lys
1               5                   10
```